(12) United States Patent
Berthel et al.

(10) Patent No.: US 8,470,866 B2
(45) Date of Patent: Jun. 25, 2013

(54) ISOINDOLINONE DERIVATIVES

(75) Inventors: Steven Joseph Berthel, Mendham Township, NJ (US); Robert Francis Kester, West Orange, NJ (US); Lucja Orzechowski, Kinnelon, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/455,169

(22) Filed: Apr. 25, 2012

(65) Prior Publication Data

US 2012/0283271 A1    Nov. 8, 2012

Related U.S. Application Data

(60) Provisional application No. 61/481,789, filed on May 3, 2011.

(51) Int. Cl.
*A61K 31/415* (2006.01)
*C07D 403/02* (2006.01)

(52) U.S. Cl.
USPC .................................. 514/404; 548/364.7

(58) Field of Classification Search
None
See application file for complete search history.

(56) References Cited

U.S. PATENT DOCUMENTS

| | | | |
|---|---|---|---|
| 6,482,951 B2 * | 11/2002 | Guertin ..................... | 548/159 |
| 2002/0082260 A1 | 6/2002 | Guertin et al. | |
| 2008/0021032 A1 | 1/2008 | Berthel et al. | |
| 2009/0163545 A1 | 6/2009 | Goldfarb et al. | |

FOREIGN PATENT DOCUMENTS

WO    2004/052869    6/2004

OTHER PUBLICATIONS

King, Medicinal Chemistry: principles and practice, 2004, 207-225.*
Wermuth, The Practice of Medicinal Chemistry, 1996, 203-237.*
Silverman, R. B., "The Organic Chemistry of Drug Design & Drug Addiction, Academic Press, San Diego, California" (Prodrugs & Drug Delivery Systems), 8:497-558 ( 2004).
International Search Report PCTEP2012057876 mailed Jun. 12, 2012.
Cahn et al., "Chem. Inter. Edit." 5:511 ( 1966).
Kumar et al., "Current Chemical Genomics" 2(1):76-89 ( 2008).

* cited by examiner

*Primary Examiner* — Noble Jarrell
*Assistant Examiner* — Laura Daniel

(57) ABSTRACT

The present invention relates to compounds of the formula I,

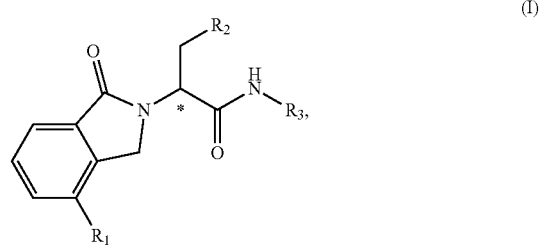

(I)

as well as pharmaceutically-acceptable salts thereof, pharmaceutical compositions containing said compounds and methods of using said compounds in the treatment or prophylaxis of diseases and disorders. The compounds and compositions disclosed herein are glucokinase activators useful for the treatment or prophylaxis of metabolic diseases and disorders, for example diabetes mellitus, including type II diabetes mellitus.

13 Claims, No Drawings

ISOINDOLINONE DERIVATIVES

PRIORITY TO RELATED APPLICATIONS

This application claims the benefit of U.S. Provisional Application No. 61/481,789, filed May 3, 2011, which is hereby incorporated by reference in its entirety.

FIELD OF THE INVENTION

The present invention relates to compounds useful as glucokinase activators for the treatment or prophylaxis of metabolic diseases and disorders.

BACKGROUND OF THE INVENTION

Glucokinase (GK), also referred to as Hexokinase IV, is one of four hexokinases that are found in mammals. Hexokinases catalyze the first step in the metabolism of glucose, i.e., the conversion of glucose to glucose-6-phosphate. GK has been found to have a critical role in whole-body glucose homeostasis. As such, activation of GK represents a potentially important therapeutic intervention point and small molecule GK activators have considerable potential for the treatment or prophylaxis of metabolic diseases and disorders, for example, Type II diabetes.

SUMMARY OF THE INVENTION

The present invention is directed in part to compounds of formula (I),

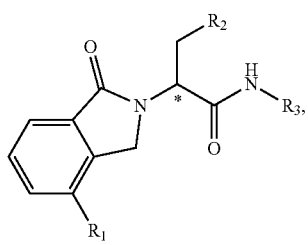

wherein:
$R_1$ is selected from the group consisting of: H, F, and $CF_3$;
$R_2$ is selected from the group consisting of: isopropyl, cyclopropyl, cyclopentyl, cyclohexyl, and $-CH_2-S-CH_3$;
$R_3$ is

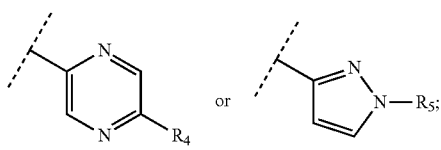

$R_4$ is selected from the group consisting of: H, Br, and $-CH(OH)-CH_2OH$; and
$R_5$ is selected from the group consisting of: $-CH(OH)-CH_2OH$, $-CH_2-C(CH_3)_2-O-CH_3$, $-CH_2-CH_2OH$, $-CH_2-C(O)-O-C(CH_3)_3$, $-(CH_2)_2O-CH_3$, $-CH_2-COOH$, $-(CH_2)_2-COOH$, $-(CH_2)_2-C(O)-O-C(CH_3)_3$, $-(CH_2)_2-CH_2OH$, $-(CH_2)_2-O-CH(CH_3)_2$, and $-CH_3$;
and wherein, when $R_3$ is

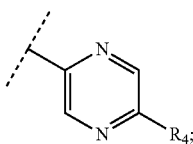

$R_1$ is $CF_3$; and
$R_2$ is selected from the group consisting of: isopropyl, cyclopentyl, and $-CH_2-S-CH_3$; and (2) when $R_3$ is

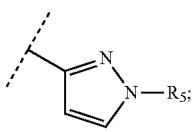

$R_1$ is selected from the group consisting of: H, F, and $CF_3$; and
$R_2$ is selected from the group consisting of: cyclopentyl, cyclohexyl, and cyclopropyl;
or a pharmaceutically-acceptable salt thereof.

The compounds are useful as glucokinase activators for the treatment or prophylaxis of metabolic diseases and disorders, for example diabetes mellitus, including type II diabetes mellitus.

The present invention also relates to a process for the preparation of a compound according to formula (I) comprising the reaction of a compound of formula (VII),

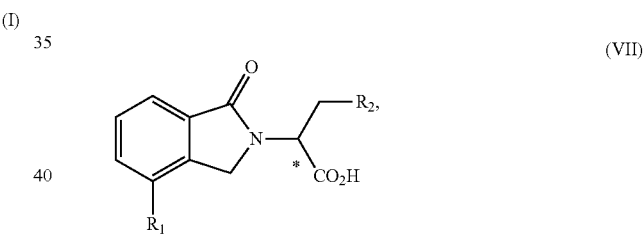

with a compound of formula (VIII), $$H_2N-R_3 \qquad (VIII),$$

wherein $R_1$, $R_2$, and $R_3$ are as previously defined.

The present invention also relates to a compound according to formula (I), or a pharmaceutically-acceptable salt thereof, for use as a therapeutically active substance.

The present invention also relates to a pharmaceutical composition, comprising a compound according to formula (I), or a pharmaceutically-acceptable salt thereof, and a pharmaceutically-acceptable carrier.

The present invention also relates to the use of a compound according to formula (I), or a pharmaceutically-acceptable salt thereof, for the treatment or prophylaxis of a metabolic disease or disorder.

The present invention also relates to the use of a compound according to formula (I), or a pharmaceutically-acceptable salt thereof, for the preparation of a medicament for the treatment or prophylaxis of a metabolic disease or disorder.

The present invention also relates to a compound according to formula (I), or a pharmaceutically-acceptable salt thereof, for the treatment or prophylaxis of a metabolic disease or disorder.

The present invention also relates to a compound according to formula (I), or a pharmaceutically-acceptable salt thereof, prepared according to the aforementioned process for preparing said compound.

The present invention also relates to a method for activating glucokinase comprising administering to a patient a therapeutically-effective amount of a compound according to formula (I), or a pharmaceutically-acceptable salt thereof.

The present invention also relates to a method for the treatment or prophylaxis of a metabolic disease or disorder, which method comprises administering to a patient in need thereof a therapeutically-effective amount of a compound according to formula (I), or a pharmaceutically-acceptable salt thereof.

DETAILED DESCRIPTION OF THE INVENTION

It is to be understood that the terminology employed herein is for the purpose of describing particular embodiments and is not intended to be limiting. Further, although any methods, devices and materials similar or equivalent to those described herein can be used in the practice or testing of the invention, the preferred methods, devices and materials are now described.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

Any open valency appearing on a carbon, oxygen, sulfur or nitrogen atom in the structures herein indicates the presence of a hydrogen, unless indicated otherwise.

The definitions described herein apply irrespective of whether the terms in question appear alone or in combination. It is contemplated that the definitions described herein may be appended to form chemically-relevant combinations, such as e.g. "heterocycloalkyl-aryl", "haloalkyl-heteroaryl", "aryl-alkyl-heterocycloalkyl", or "alkoxy-alkyl". The last member of the combination is a radical which is substituted by the other members of the combination in inverse order.

The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "compound(s) of this invention" and "compound(s) of the present invention" refers to compounds of formula I and stereoisomers, tautomers, solvates, and salts (e.g., pharmaceutically acceptable salts) thereof.

It will be appreciated, that the compounds of present invention may be derivatized at functional groups to provide derivatives which are capable of conversion back to the parent compound in vivo. Physiologically acceptable and metabolically labile derivatives, which are capable of producing the parent compounds of present invention in vivo are also within the scope of this invention.

The term "prodrug" denotes a form or derivative of a compound which is metabolized in vivo, e.g., by biological fluids or enzymes by a subject after administration, into a pharmacologically active form of the compound in order to produce the desired pharmacological effect. Prodrugs are described e.g. in "The Organic Chemistry of Drug Design and Drug Action", by Richard B. Silverman, Academic Press, San Diego, 2004, Chapter 8 Prodrugs and Drug Delivery Systems, pp. 497-558.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins.

The term "solvate" denotes crystal forms having either stoichiometric or nonstoichiometric amounts of a solvent incorporated in the crystal lattice. If the incorporated solvent is water, the solvate formed is a hydrate. When the incorporated solvent is alcohol, the solvate formed is an alcoholate.

Structures depicted herein are also meant to include compounds that differ only in the presence of one or more isotopically enriched atoms. For example wherein one or more hydrogen atoms are replaced by deuterium, or one or more carbon atoms are replaced by a 13C- or 14C-enriched carbon are within the scope of this invention.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The term "stereoisomer" denotes a compound that possesses identical molecular connectivity and bond multiplicity, but which differs in the arrangement of its atoms in space.

The term "chiral center" denotes a carbon atom bonded to four nonidentical substituents. The term "chiral" denotes the ability of non-superimposability with the mirror image, while the term "achiral" refers to embodiments which are superimposable with their mirror image. Chiral molecules are optically active, i.e., they have the ability to rotate the plane of plane-polarized light.

Compounds of present invention can have one or more chiral centers and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. Whenever a chiral center is present in a chemical structure, it is intended that all stereoisomers associated with that chiral center are encompassed by the present invention.

The term "enantiomers" denotes two stereoisomers of a compound which are non-superimposable mirror images of one another.

The term "diastereomer" denotes a stereoisomer with two or more centers of chirality and whose molecules are not mirror images of one another. Diastereomers have different physical properties, e.g. melting points, boiling points, spectral properties, and reactivities.

The term "racemate" or "racemic mixture" refers to an equimolar mixture of two enantiomeric species, devoid of optical activity.

The term "alkyl" denotes a monovalent linear or branched saturated hydrocarbon group of 1 to 12 carbon atoms, in particular of 1 to 7 carbon atoms, more particular of 1 to 4 carbon atoms, for example, methyl, ethyl, propyl, isopropyl, n-butyl, iso-butyl, sec-butyl, or tert-butyl.

The term "active pharmaceutical ingredient" (or "API") denotes the compound in a pharmaceutical composition that has a particular biological activity.

The term "pharmaceutically-acceptable" denotes an attribute of a material which is useful in preparing a pharmaceutical composition that is generally safe, non-toxic, and neither biologically nor otherwise undesirable and is acceptable for veterinary as well as human pharmaceutical use.

The term "pharmaceutically-acceptable excipient" denotes any ingredient having no therapeutic activity and being non-toxic such as disintegrators, binders, fillers, solvents, buffers, tonicity agents, stabilizers, antioxidants, surfactants or lubricants used in formulating pharmaceutical products.

The term "pharmaceutical composition" (or "composition") denotes a mixture or solution comprising a therapeutically effective amount of an active pharmaceutical ingredient together with pharmaceutically acceptable-excipients to be administered to a mammal, e.g., a human in need thereof.

The term "lyophilization" and variations thereof (e.g., "lyophilized") refers to the process of freezing a substance and then reducing the concentration of water, by sublimation and/or evaporation to levels which do not support biological or chemical reactions.

The term "reconstituted composition" in connection with the composition according to the invention denotes a lyophilized composition which is re-dissolved by addition of reconstitution medium. The reconstitution medium comprises water for injection (WFI), bacteriostatic water for injection (BWFI), sodium chloride solutions (e.g. 0.9% (w/v) NaCl), glucose solutions (e.g. 5% glucose), surfactant comprising solutions (e.g. 0.01% polysorbate 20), or pH-buffered solution (e.g. phosphate-buffered solutions).

The term "sterile" denotes that a composition or excipient has a probability of being microbially contaminated of less than $10^{-6}$.

The term "buffer" denotes a pharmaceutically acceptable excipient, which stabilizes the pH of a pharmaceutical preparation. Suitable buffers are well known in the art and can be found in the literature. Particular pharmaceutically acceptable buffers comprise histidine-buffers, arginine-buffers, citrate-buffers, succinate-buffers, acetate-buffers and phosphate-buffers. Independently from the buffer used, the pH can be adjusted with an acid or a base known in the art, e.g. hydrochloric acid, acetic acid, phosphoric acid, sulfuric acid and citric acid, sodium hydroxide and potassium hydroxide.

The term "tonicity" denotes a measure of the osmotic pressure of two solutions separated by a semi-permeable membrane. Osmotic pressure is the pressure that must be applied to a solution to prevent the inward flow of water across a semi-permeable membrane. Osmotic pressure and tonicity are influenced only by solutes that cannot cross the membrane, as only these exert an osmotic pressure. Solutes able to freely cross the membrane do not affect tonicity because they will always be in equal concentrations on both sides of the membrane.

Tonicity in general relates to the osmotic pressure of a solution usually relative to that of human blood serum. A composition can be hypotonic, isotonic or hypertonic. An isotonic composition is liquid or liquid reconstituted from a solid form, e.g. from a lyophilized form, and denotes a solution having the same tonicity as some other solution with which it is compared, such as physiologic salt solution and the blood serum.

The term "surfactant" denotes a pharmaceutically acceptable excipient which is used to protect protein compositions against mechanical stresses like agitation and shearing. Examples of pharmaceutically acceptable surfactants include poloxamers, polysorbates, polyoxyethylene alkyl ethers (Brij), alkylphenylpolyoxyethylene ethers (Triton-X) or sodium dodecyl sulfate (SDS).

The term "poloxamer" denotes non-ionic triblock copolymers composed of a central hydrophobic chain of poly(propylene oxide) (PPO) flanked by two hydrophilic chains of poly(ethylene oxide) (PEO), each PPO or PEO chain can be of different molecular weights. Poloxamers are also known by the trade name Pluronics. Particular Poloxamer is Poloxamer 188, a poloxamer wherein the PPO chain has a molecular mass of 1800 g/mol and a PEO content of 80% (w/w).

The term "polysorbate" denotes oleate esters of sorbitol and its anhydrides, typically copolymerized with ethylene oxide. Particular polysorbates are Polysorbate 20 (poly(ethylene oxide) (20) sorbitan monolaurate, Tween 20) or Polysorbate 80 (poly(ethylene oxide) (80) sorbitan monolaurate, Tween 80).

The term "antioxidant" denotes pharmaceutically acceptable excipients, which prevent oxidation of the active pharmaceutical ingredient. Antioxidants comprise ascorbic acid, glutathione, cysteine, methionine, citric acid, EDTA.

The term "tonicity agent" denotes pharmaceutically acceptable excipient used to modulate the tonicity of a composition. Suitable tonicity agents comprise amino acids and sugars. Particular tonicity agents are trehalose, sucrose or arginine.

The term "sugar" denotes a monosaccharide or an oligosaccharide. A monosaccharide is a monomeric carbohydrate which is not hydrolysable by acids, including simple sugars and their derivatives, e.g. aminosugars. Examples of monosaccharides include glucose, fructose, galactose, mannose, sorbose, ribose, deoxyribose, neuraminic acid. An oligosaccharide is a carbohydrate consisting of more than one monomeric saccharide unit connected via glycosidic bond(s) either branched or in a chain. The monomeric saccharide units within an oligosaccharide can be identical or different. Depending on the number of monomeric saccharide units the oligosaccharide is a di-, tri-, tetra- penta- and so forth saccharide. In contrast to polysaccharides the monosaccharides and oligosaccharides are water soluble. Examples of oligosaccharides include sucrose, trehalose, lactose, maltose and raffinose.

The term "treating" or "treatment" of a disease state includes (1) preventing the disease state, i.e. causing the clinical symptoms of the disease state not to develop in a subject that may be exposed to or predisposed to the disease state, but does not yet experience or display symptoms of the disease state, (2) inhibiting the disease state, i.e., arresting the development of the disease state or its clinical symptoms, or (3) relieving the disease state, i.e., causing temporary or permanent regression of the disease state or its clinical symptoms.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity of the disease treated, the age and relative health of the subject, the route and form of administration, the judgment of the attending medical or veterinary practitioner, and other factors.

The term "subject" denotes a vertebrate. In certain embodiments, the vertebrate is a mammal Mammals include humans, non-human primates such as chimpanzees and other apes and monkey species, farm animals such as cattle, horses, sheep, goats, and swine, domestic animals such as rabbits, dogs, and cats, laboratory animals including rodents, such as rats, mice, and guinea pigs. In certain embodiments, a mammal is a human. The term subject does not denote a particular age or sex.

In an embodiment of the present invention, provided are compound of formula (I):

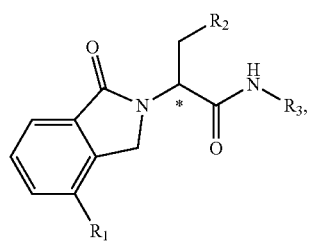

(I)

wherein:
$R_1$ is selected from the group consisting of: H, F, and $CF_3$;
$R_2$ is selected from the group consisting of: isopropyl, cyclopropyl, cyclopentyl, cyclohexyl, and —$CH_2$—S—$CH_3$;
$R_3$ is

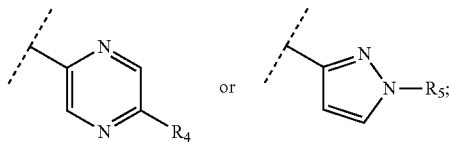

$R_4$ is selected from the group consisting of: H, Br, and —CH(OH)—$CH_2OH$; and
$R_5$ is selected from the group consisting of: —CH(OH)—$CH_2OH$, —$CH_2$—$C(CH_3)_2$—O—$CH_3$, —$CH_2$—$CH_2OH$, —$CH_2$—C(O)—O—$C(CH_3)_3$, —$(CH_2)_2O$—$CH_3$, —$CH_2$—COOH, —$(CH_2)_2$—COOH, —$(CH_2)_2$—C(O)—O—$C(CH_3)_3$, —$(CH_2)_2$—$CH_2OH$, —$(CH_2)_2$—O—$CH(CH_3)_2$, and —$CH_3$;
and wherein,
when $R_3$ is

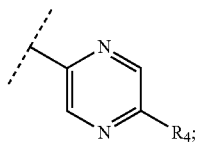

$R_1$ is $CF_3$; and
$R_2$ is selected from the group consisting of: isopropyl, cyclopentyl, and —$CH_2$—S—$CH_3$; and (2) when $R_3$ is

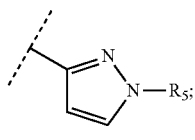

$R_1$ is selected from the group consisting of: H, F, and $CF_3$; and
$R_2$ is selected from the group consisting of: cyclopentyl, cyclohexyl, and cyclopropyl;
or a pharmaceutically-acceptable salt of said compound.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

In the compound of formula I, the asterisk denotes an asymmetric carbon atom. The compound of formula I may be present as a racemate or in either the R or S configurations. In a particular embodiment of the present invention, the compound is in the S configuration.

In an embodiment, the compound is a compound of formula (I), wherein $R_3$ is

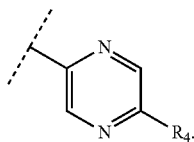

In an embodiment, the compound is a compound of formula (I) selected from the group consisting of:
(S)-3-cyclopentyl-2-(1-oxo-4-trifluoromethyl-1,3-dihydro-isoindol-2-yl)-N-pyrazin-2-yl-propionamide;
(S)—N-(5-bromo-pyrazin-2-yl)-3-cyclopentyl-2-(1-oxo-4-trifluoromethyl-1,3-dihydro-isoindol-2-yl)-propionamide;
(S)-3-cyclopentyl-N-[5-((S)-1,2-dihydroxy-ethyl)-pyrazin-2-yl]-2-(1-oxo-4-trifluoromethyl-1,3-dihydro-isoindol-2-yl)-propionamide;
(S)—N-[5-((S)-1,2-dihydroxy-ethyl)-pyrazin-2-yl]-4-methylsulfanyl-2-(1-oxo-4-trifluoromethyl-1,3-dihydro-isoindol-2-yl)-butyramide;
(S)-4-methyl-2-(1-oxo-4-trifluoromethyl-1,3-dihydro-isoindol-2-yl)-pentanoic acid pyrazin-2-ylamide;
(S)-4-methyl-2-(1-oxo-4-trifluoromethyl-1,3-dihydro-isoindol-2-yl)-pentanoic acid [5-((S)-1,2-dihydroxy-ethyl)-pyrazin-2-yl]-amide;
and pharmaceutically-acceptable salts thereof.

In an embodiment, the compound is a compound of formula (I), wherein $R_3$ is

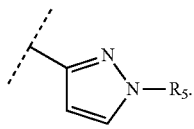

In an embodiment, the compound is a compound of formula (I) selected from the group consisting of:
(S)-3-cyclopentyl-N-(1-methyl-1H-pyrazol-3-yl)-2-(1-oxo-4-trifluoromethyl-1,3-dihydro-isoindol-2-yl)-propionamide;
(S)-3-cyclopentyl-N-[1-(2-hydroxy-ethyl)-1H-pyrazol-3-yl]-2-(1-oxo-4-trifluoromethyl-1,3-dihydro-isoindol-2-yl)-propionamide;
{3-[(S)-3-cyclopentyl-2-(1-oxo-4-trifluoromethyl-1,3-dihydro-isoindol-2-yl)-propionylamino]-pyrazol-1-yl}-acetic acid tert-butyl ester;
{3-[(S)-3-cyclopentyl-2-(1-oxo-4-trifluoromethyl-1,3-dihydro-isoindol-2-yl)-propionylamino]-pyrazol-1-yl}-acetic acid;
(S)-3-cyclopentyl-N-[1-((R)-2,3-dihydroxy-propyl)-1H-pyrazol-3-yl]-2-(1-oxo-4-trifluoromethyl-1,3-dihydro-isoindol-2-yl)-propionamide;
(S)-3-cyclopentyl-N-[1-((S)-2,3-dihydroxy-propyl)-1H-pyrazol-3-yl]-2-(1-oxo-4-trifluoromethyl-1,3-dihydro-isoindol-2-yl)-propionamide;
(S)-3-cyclopentyl-N-[1-(2-methoxy-2-methyl-propyl)-1H-pyrazol-3-yl]-2-(1-oxo-4-trifluoromethyl-1,3-dihydro-isoindol-2-yl)-propionamide;
(S)-3-cyclohexyl-N-[1-(2-methoxy-ethyl)-1H-pyrazol-3-yl]-2-(1-oxo-1,3-dihydro-isoindol-2-yl)-propionamide;
(S)-3-cyclopentyl-N-[1-(2-methoxy-ethyl)-1H-pyrazol-3-yl]-2-(1-oxo-1,3-dihydro-isoindol-2-yl)-propionamide;
(S)-3-cyclopropyl-N-[1-(2-methoxy-2-methyl-propyl)-1H-pyrazol-3-yl]-2-(1-oxo-1,3-dihydro-isoindol-2-yl)-propionamide;
(S)-3-cyclopentyl-N-[1-(2-isopropoxy-ethyl)-1H-pyrazol-3-yl]-2-(1-oxo-1,3-dihydro-isoindol-2-yl)-propionamide;
(S)-3-cyclopentyl-N-[1-(3-hydroxy-propyl)-1H-pyrazol-3-yl]-2-(1-oxo-1,3-dihydro-isoindol-2-yl)-propionamide;
(S)-3-cyclopentyl-N-[1-(2-methoxy-ethyl)-1H-pyrazol-3-yl]-2-(1-oxo-4-trifluoromethyl-1,3-dihydro-isoindol-2-yl)-propionamide;
(S)-3-cyclopentyl-N-[1-(2-methoxy-2-methyl-propyl)-1H-pyrazol-3-yl]-2-(1-oxo-1,3-dihydro-isoindol-2-yl)-propionamide;
(S)-3-cyclopentyl-N-[1-(2-isopropoy-ethyl)-1H-pyrazol-3-yl]-2-(1-oxo-4-trifluoromethyl-1,3-dihydro-isoindol-2-yl)-propionamide;
(S)-3-cyclohexyl-2-(4-fluoro-1-oxo-1,3-dihydro-isoindol-2-yl)-N-[1-(2-methoxy-ethyl)-1H-pyrazol-3-yl]-propionamide;
3-{3-[(S)-3-cyclopentyl-2-(1-oxo-4-trifluoromethyl-1,3-dihydro-isoindol-2-yl)-propionylamino]-pyrazol-1-yl}-propionic acid tert-butyl ester;
3-{3-[(S)-3-cyclopentyl-2-(1-oxo-4-trifluoromethyl-1,3-dihydro-isoindol-2-yl)-propionylamino]-pyrazol-1-yl}-propionic acid;
and pharmaceutically-acceptable salts thereof.

In an embodiment, the compound is a compound of formula (I), wherein $R_1$ is $CF_3$.

In an embodiment, the compound is a compound of formula (I), selected from the group consisting of:
(S)-3-cyclopentyl-N-(1-methyl-1H-pyrazol-3-yl)-2-(1-oxo-4-trifluoromethyl-1,3-dihydro-isoindol-2-yl)-propionamide;
(S)-3-cyclopentyl-N-[1-(2-hydroxy-ethyl)-1H-pyrazol-3-yl]-2-(1-oxo-4-trifluoromethyl-1,3-dihydro-isoindol-2-yl)-propionamide;
{3-[(S)-3-cyclopentyl-2-(1-oxo-4-trifluoromethyl-1,3-dihydro-isoindol-2-yl)-propionylamino]-pyrazol-1-yl}-acetic acid tert-butyl ester;
{3-[(S)-3-cyclopentyl-2-(1-oxo-4-trifluoromethyl-1,3-dihydro-isoindol-2-yl)-propionylamino]-pyrazol-1-yl}-acetic acid;
(S)-3-cyclopentyl-N-[1-((R)-2,3-dihydroxy-propyl)-1H-pyrazol-3-yl]-2-(1-oxo-4-trifluoromethyl-1,3-dihydro-isoindol-2-yl)-propionamide;
(S)-3-cyclopentyl-N-[1-((S)-2,3-dihydroxy-propyl)-1H-pyrazol-3-yl]-2-(1-oxo-4-trifluoromethyl-1,3-dihydro-isoindol-2-yl)-propionamide;
(S)-3-cyclopentyl-N-[1-(2-methoxy-2-methyl-propyl)-1H-pyrazol-3-yl]-2-(1-oxo-4-trifluoromethyl-1,3-dihydro-isoindol-2-yl)-propionamide;
(S)-3-cyclopentyl-N-[1-(2-methoxy-ethyl)-1H-pyrazol-3-yl]-2-(1-oxo-4-trifluoromethyl-1,3-dihydro-isoindol-2-yl)-propionamide;
(S)-3-cyclopentyl-2-(1-oxo-4-trifluoromethyl-1,3-dihydro-isoindol-2-yl)-N-pyrazin-2-yl-propionamide;
(S)—N-(5-bromo-pyrazin-2-yl)-3-cyclopentyl-2-(1-oxo-4-trifluoromethyl-1,3-dihydro-isoindol-2-yl)-propionamide;
(S)-3-cyclopentyl-N-[1-(2-isopropoy-ethyl)-1H-pyrazol-3-yl]-2-(1-oxo-4-trifluoromethyl-1,3-dihydro-isoindol-2-yl)-propionamide;
3-{3-[(S)-3-cyclopentyl-2-(1-oxo-4-trifluoromethyl-1,3-dihydro-isoindol-2-yl)-propionylamino]-pyrazol-1-yl}-propionic acid tert-butyl ester;

3-{3-[(S)-3-cyclopentyl-2-(1-oxo-4-trifluoromethyl-1,3-dihydro-isoindol-2-yl)-propionylamino]-pyrazol-1-yl}-propionic acid;
(S)-3-cyclopentyl-N-[5-((S)-1,2-dihydroxy-ethyl)-pyrazin-2-yl]-2-(1-oxo-4-trifluoromethyl-1,3-dihydro-isoindol-2-yl)-propionamide;
(S)—N-[5-((S)-1,2-dihydroxy-ethyl)-pyrazin-2-yl]-4-methylsulfanyl-2-(1-oxo-4-trifluoromethyl-1,3-dihydro-isoindol-2-yl)-butyramide;
(S)-4-methyl-2-(1-oxo-4-trifluoromethyl-1,3-dihydro-isoindol-2-yl)-pentanoic acid pyrazin-2-ylamide;
(S)-4-methyl-2-(1-oxo-4-trifluoromethyl-1,3-dihydro-isoindol-2-yl)-pentanoic acid [5-((S)-1,2-dihydroxy-ethyl)-pyrazin-2-yl]-amide;
and pharmaceutically-acceptable salts thereof.

In an embodiment, the compound is a compound of formula (I), wherein $R_2$ is cyclopentyl.

In an embodiment, the compound is a compound of formula (I), selected from the group consisting of:
(S)-3-cyclopentyl-N-(1-methyl-1H-pyrazol-3-yl)-2-(1-oxo-4-trifluoromethyl-1,3-dihydro-isoindol-2-yl)-propionamide;
(S)-3-cyclopentyl-N-[1-(2-hydroxy-ethyl)-1H-pyrazol-3-yl]-2-(1-oxo-4-trifluoromethyl-1,3-dihydro-isoindol-2-yl)-propionamide;
{3-[(S)-3-cyclopentyl-2-(1-oxo-4-trifluoromethyl-1,3-dihydro-isoindol-2-yl)-propionylamino]-pyrazol-1-yl}-acetic acid tert-butyl ester;
{3-[(S)-3-cyclopentyl-2-(1-oxo-4-trifluoromethyl-1,3-dihydro-isoindol-2-yl)-propionylamino]-pyrazol-1-yl}-acetic acid;
(S)-3-cyclopentyl-N-[1-((R)-2,3-dihydroxy-propyl)-1H-pyrazol-3-yl]-2-(1-oxo-4-trifluoromethyl-1,3-dihydro-isoindol-2-yl)-propionamide;
(S)-3-cyclopentyl-N-[1-((S)-2,3-dihydroxy-propyl)-1H-pyrazol-3-yl]-2-(1-oxo-4-trifluoromethyl-1,3-dihydro-isoindol-2-yl)-propionamide;
(S)-3-cyclopentyl-N-[1-(2-methoxy-2-methyl-propyl)-1H-pyrazol-3-yl]-2-(1-oxo-4-trifluoromethyl-1,3-dihydro-isoindol-2-yl)-propionamide;
(S)-3-cyclopentyl-N-[1-(2-methoxy-ethyl)-1H-pyrazol-3-yl]-2-(1-oxo-1,3-dihydro-isoindol-2-yl)-propionamide;
(S)-3-cyclopentyl-N-[1-(2-isopropoxy-ethyl)-1H-pyrazol-3-yl]-2-(1-oxo-1,3-dihydro-isoindol-2-yl)-propionamide;
(S)-3-cyclopentyl-N-[1-(3-hydroxy-propyl)-1H-pyrazol-3-yl]-2-(1-oxo-1,3-dihydro-isoindol-2-yl)-propionamide;
(S)-3-cyclopentyl-N-[1-(2-methoxy-ethyl)-1H-pyrazol-3-yl]-2-(1-oxo-4-trifluoromethyl-1,3-dihydro-isoindol-2-yl)-propionamide;
(S)-3-cyclopentyl-N-[1-(2-methoxy-2-methyl-propyl)-1H-pyrazol-3-yl]-2-(1-oxo-1,3-dihydro-isoindol-2-yl)-propionamide;
(S)-3-cyclopentyl-2-(1-oxo-4-trifluoromethyl-1,3-dihydro-isoindol-2-yl)-N-pyrazin-2-yl-propionamide;
(S)—N-(5-bromo-pyrazin-2-yl)-3-cyclopentyl-2-(1-oxo-4-trifluoromethyl-1,3-dihydro-isoindol-2-yl)-propionamide;
(S)-3-cyclopentyl-N-[1-(2-isopropoy-ethyl)-1H-pyrazol-3-yl]-2-(1-oxo-4-trifluoromethyl-1,3-dihydro-isoindol-2-yl)-propionamide;
3-{3-[(S)-3-cyclopentyl-2-(1-oxo-4-trifluoromethyl-1,3-dihydro-isoindol-2-yl)-propionylamino]-pyrazol-1-yl}-propionic acid tert-butyl ester;
3-{3-[(S)-3-cyclopentyl-2-(1-oxo-4-trifluoromethyl-1,3-dihydro-isoindol-2-yl)-propionylamino]-pyrazol-1-yl}-propionic acid;
(S)-3-cyclopentyl-N-[5-((S)-1,2-dihydroxy-ethyl)-pyrazin-2-yl]-2-(1-oxo-4-trifluoromethyl-1,3-dihydro-isoindol-2-yl)-propionamide;
and pharmaceutically-acceptable salts thereof.

In an embodiment, the compound is a compound of formula (I), wherein $R_1$ is H.

In an embodiment, the compound is a compound of formula (I), selected from the group consisting of:
(S)-3-cyclohexyl-N-[1-(2-methoxy-ethyl)-1H-pyrazol-3-yl]-2-(1-oxo-1,3-dihydro-isoindol-2-yl)-propionamide;
(S)-3-cyclopentyl-N-[1-(2-methoxy-ethyl)-1H-pyrazol-3-yl]-2-(1-oxo-1,3-dihydro-isoindol-2-yl)-propionamide;
(S)-3-cyclopropyl-N-[1-(2-methoxy-2-methyl-propyl)-1H-pyrazol-3-yl]-2-(1-oxo-1,3-dihydro-isoindol-2-yl)-propionamide;
(S)-3-cyclopentyl-N-[1-(2-isopropoxy-ethyl)-1H-pyrazol-3-yl]-2-(1-oxo-1,3-dihydro-isoindol-2-yl)-propionamide;
(S)-3-cyclopentyl-N-[1-(3-hydroxy-propyl)-1H-pyrazol-3-yl]-2-(1-oxo-1,3-dihydro-isoindol-2-yl)-propionamide;
(S)-3-cyclopentyl-N-[1-(2-methoxy-2-methyl-propyl)-1H-pyrazol-3-yl]-2-(1-oxo-1,3-dihydro-isoindol-2-yl)-propionamide;
and pharmaceutically-acceptable salts thereof.

In an embodiment, the compound is a compound of formula (I), wherein $R_1$ is $CF_3$, $R_2$ is cyclopentyl, and $R_3$ is

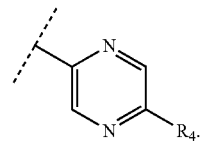

In an embodiment, the compound is a compound of formula (I) selected from the group consisting of:
(S)-3-cyclopentyl-2-(1-oxo-4-trifluoromethyl-1,3-dihydro-isoindol-2-yl)-N-pyrazin-2-yl-propionamide;
(S)—N-(5-bromo-pyrazin-2-yl)-3-cyclopentyl-2-(1-oxo-4-trifluoromethyl-1,3-dihydro-isoindol-2-yl)-propionamide;
(S)-3-cyclopentyl-N-[5-((S)-1,2-dihydroxy-ethyl)-pyrazin-2-yl]-2-(1-oxo-4-trifluoromethyl-1,3-dihydro-isoindol-2-yl)-propionamide;
and pharmaceutically-acceptable salts thereof.

In an embodiment, the compound is a compound of formula (I), wherein $R_1$ is $CF_3$, $R_2$ is cyclopentyl, and $R_3$ is

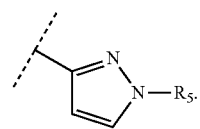

In an embodiment, the compound is a compound of formula (I) selected from the group consisting of:
(S)-3-cyclopentyl-N-(1-methyl-1H-pyrazol-3-yl)-2-(1-oxo-4-trifluoromethyl-1,3-dihydro-isoindol-2-yl)-propionamide;
(S)-3-cyclopentyl-N-[1-(2-hydroxy-ethyl)-1H-pyrazol-3-yl]-2-(1-oxo-4-trifluoromethyl-1,3-dihydro-isoindol-2-yl)-propionamide;
{3-[(S)-3-cyclopentyl-2-(1-oxo-4-trifluoromethyl-1,3-dihydro-isoindol-2-yl)-propionylamino]-pyrazol-1-yl}-acetic acid tert-butyl ester;

{3-[(S)-3-cyclopentyl-2-(1-oxo-4-trifluoromethyl-1,3-dihydro-isoindol-2-yl)-propionylamino]-pyrazol-1-yl}-acetic acid;

(S)-3-cyclopentyl-N-[1-((R)-2,3-dihydroxy-propyl)-1H-pyrazol-3-yl]-2-(1-oxo-4-trifluoromethyl-1,3-dihydro-isoindol-2-yl)-propionamide;

(S)-3-cyclopentyl-N-[1-((S)-2,3-dihydroxy-propyl)-1H-pyrazol-3-yl]-2-(1-oxo-4-trifluoromethyl-1,3-dihydro-isoindol-2-yl)-propionamide;

(S)-3-cyclopentyl-N-[1-(2-methoxy-2-methyl-propyl)-1H-pyrazol-3-yl]-2-(1-oxo-4-trifluoromethyl-1,3-dihydro-isoindol-2-yl)-propionamide;

(S)-3-cyclopentyl-N-[1-(2-methoxy-ethyl)-1H-pyrazol-3-yl]-2-(1-oxo-4-trifluoromethyl-1,3-dihydro-isoindol-2-yl)-propionamide;

(S)-3-cyclopentyl-N-[1-(2-isopropoy-ethyl)-1H-pyrazol-3-yl]-2-(1-oxo-4-trifluoromethyl-1,3-dihydro-isoindol-2-yl)-propionamide;

3-{3-[(S)-3-cyclopentyl-2-(1-oxo-4-trifluoromethyl-1,3-dihydro-isoindol-2-yl)-propionylamino]-pyrazol-1-yl}-propionic acid tert-butyl ester;

3-{3-[(S)-3-cyclopentyl-2-(1-oxo-4-trifluoromethyl-1,3-dihydro-isoindol-2-yl)-propionylamino]-pyrazol-1-yl}-propionic acid;

and pharmaceutically-acceptable salts thereof.

In an embodiment of the present invention, there is provided a compound according to formula (I), or a pharmaceutically acceptable-salt thereof, for use as a therapeutically active substance, for example, for the treatment of a metabolic disease or disorder.

In another embodiment of the present invention, there is provided the use of a compound according to formula (I), or a pharmaceutically-acceptable salt thereof, for the treatment or prophylaxis of a metabolic disease or disorder.

The invention further provides the use of a compound according to formula (I), or a pharmaceutically-acceptable salt thereof, for the preparation of a medicament for the treatment or prophylaxis of a metabolic disease or disorder.

The invention further provides a compound according to formula (I), or a pharmaceutically-acceptable salt thereof, for the treatment or prophylaxis of a metabolic disease or disorder.

The present invention also relates to a method for the treatment or prophylaxis of a metabolic disease or disorder, which method comprises administering to a patient in need thereof a therapeutically-effective amount of a compound according to formula (I), or a pharmaceutically-acceptable salt thereof.

In an embodiment of the present invention, the compound according to formula (I), or a pharmaceutically-acceptable salt thereof, is administered at a dose that is within the range of from about 1 to about 1000 mg per day, in particular from about 1 mg to about 500 mg per day.

In the practice of the method of the present invention, a compound according to formula (I), or a pharmaceutically-acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The pharmaceutical composition can also be in the form of an oil emulsion or dispersion in conjunction with a lipophilic salt such as pamoic acid, or in the form of a biodegradable sustained-release composition for subcutaneous or intramuscular administration.

The present invention provides a pharmaceutical composition, comprising of a compound according to formula (I), or a pharmaceutically-acceptable salt thereof, and a pharmaceutically-acceptable carrier.

Useful pharmaceutically-acceptable carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutically-acceptable excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain a therapeutically-effective amount of the compound according to formula (I), or a pharmaceutically-acceptable salt thereof and a pharmaceutically-acceptable carrier so as to prepare the proper dosage form for proper administration to the recipient.

Compounds of formula I can be prepared as outlined in the general scheme below. Compounds of formula II (where $R_1$ is F or $CF_3$) may be treated with hydrochloric acid in methanol at reflux to produce compounds of formula III. Compounds of formula III may then be treated with N-bromosuccinimide in carbon tetrachloride with catalytic benzoyl peroxide, at 80° C., to produce compounds of formula IV. Compounds of formula IV may then be treated with compounds of formula V and triethylamine in acetonitrile in a microwave reactor at 110° C. to produce a compound of formula VI. Alternatively, compounds of formula IV may be treated with ammonia in methanol to produce compounds of formula IX. Compounds of formula IX may be treated sodium hydride in tetrahydrofuran, followed by a compound of formula X, to produce a compound of formula VI. Compounds of formula VI may be saponified using lithium hydroxide in water/tetrahydrofuran to produce a compound of formula VII (where $R_1$=F or $CF_3$). Alternatively, compounds of formula VII (where $R_1$=H) can be prepared by treating phthalic dicarboxaldehyde (XI) with a compound of formula XII. The compound of formula VII may be treated with oxalyl chloride in dichloromethane with a catalytic amount of dimethylformamide followed by a compound of formula VIII in dichloromethane with 2,6-lutidine at room temperature to produce a compounds of formula I. Alternatively, compounds of formula VII may be treated with benzotriazole-1-yl-oxy-tris-(dimethylamino)-phosphonium hexafluorophosphate and N,N-diisopropylethylamine along with compounds of formula VIII in dichloromethane to produce a compounds of formula I.

Compounds of the present invention can be prepared beginning with commercially available starting materials and utilizing general synthetic techniques and procedures known to those skilled in the art.

Compounds of formula II (2-fluoro-3-trifluoromethyl-benzoic acid and 2-methyl-3-trifluoromethyl-benzoic acid) are commercially available (Oakwood, Alfa, Apollo). Compounds of formula (V) are commercially available (Aldrich, Sigma, Alfa, Bachem, Chemimpex) or can be prepared from the corresponding amino acid or protected amino acid derivatives using standard conditions. Amino acids (XII) can be purchased (Aldrich, Sigma, Alfa, Bachem, Chemimpex) or prepared using any number of standard methods. Compounds of formula X are commercially available (Aldrich, Pfaltz & Bauer, ArkPharm) or can be prepared by brominating the corresponding methyl ester using standard conditions. The corresponding methyl esters are commercially available (Aldrich, Pfaltz & Bauer, ArkPharm), or can be prepared from the corresponding acids using standard conditions. Phthalic dicarboxaldehyde (XI) is commercially (Sigma Aldrich). Compounds of formula VIII are commercially available (Matrix, Alfa, Oakwood) or can be prepared as described in US 20080021032 or WO2004052869.

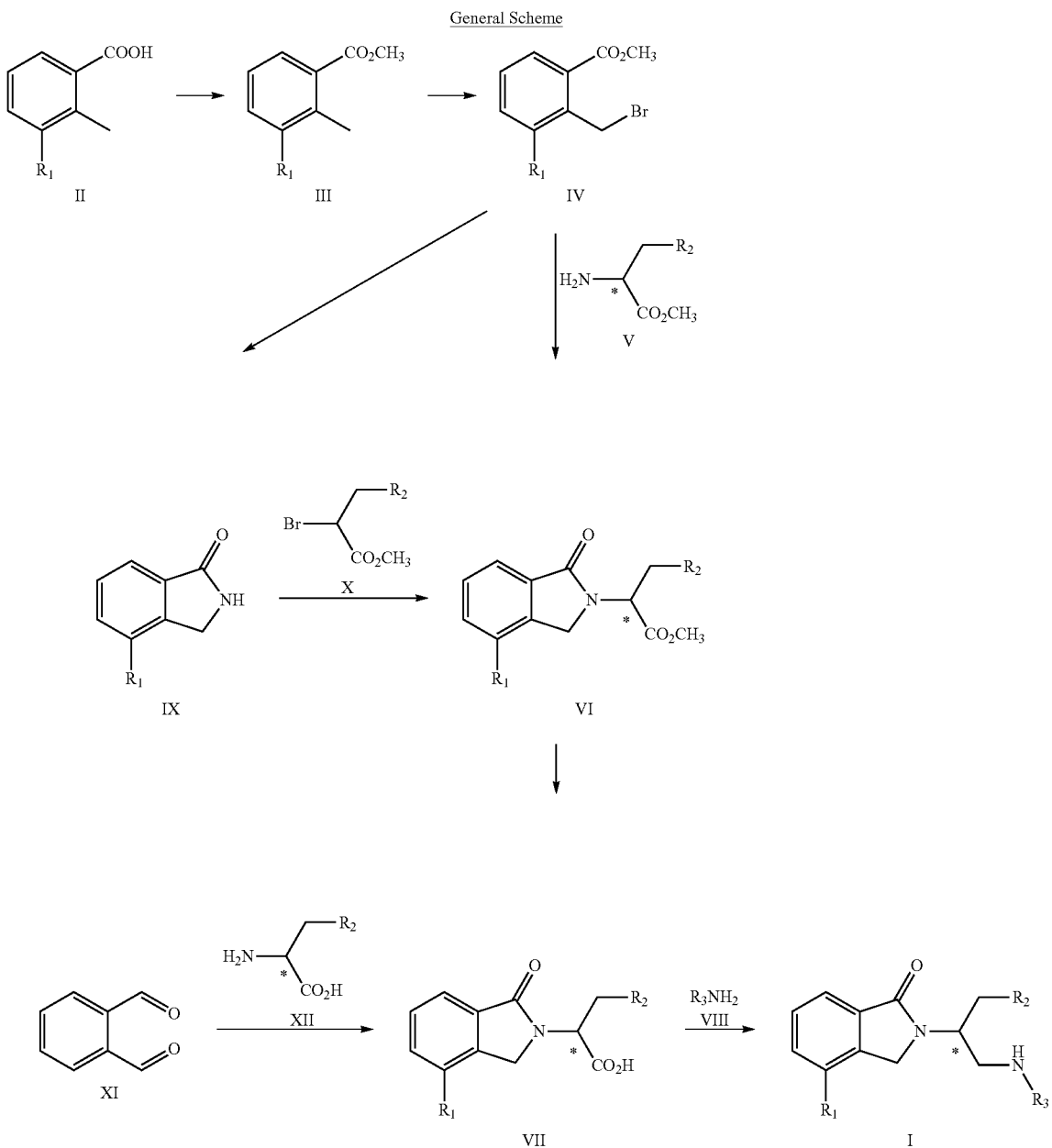

General Scheme

In an embodiment of the present invention, there is provided a process for the preparation of a compound of formula (I) or a pharmaceutically-acceptable salt thereof comprising the reaction of a compound of formula (VII), as described above, with a compound of formula (VIII), as described above. $R_1$, $R_2$, and $R_3$ are as previously defined.

An embodiment of the present invention is a process for the preparation of a compound according to formula (I) comprising the reaction of a compound of formula (VII),

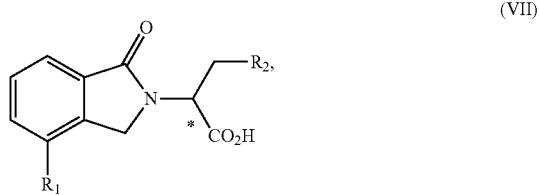

with a compound of formula (VIII), $H_2N-R_3$, wherein $R_1$, $R_2$, and $R_3$ are as previously defined.

In addition, the invention provides a compound of formula (I), or a pharmaceutically-acceptable salt thereof, manufactured according to the above process.

EXAMPLES

This invention will be more fully understood by reference to the following examples. They should not, however, be construed as limiting the scope of the invention.

Chemistry. All nonaqueous reactions were carried out under an argon or nitrogen atmosphere at room temperature, unless otherwise noted. All reagents and anhydrous solvents were used as obtained commercially without further purification or distillation, unless otherwise stated. Analytical thin-layer chromatography (TLC) was performed on EMD Chemicals silica gel 60 F254 precoated plates (0.25 mm) Compounds were visualized by UV light and/or stained with either p-anisaldehyde, iodine, or phosphomolybdic acid or $KMnO_4$ solutions followed by heating. Analytical high performance liquid chromatography (HPLC) and LC-MS analyses were conducted using the following two instruments and conditions. Method 1: Hewlett-Packard HP-1090 pump and HP-1090 PDA detector set at 215 nm with the MS detection performed with a Micromass Platform II mass spectrometer with electrospray ionization (ESI); Chromegabond WR C18 3 μm, 120 Å, 3.2×30 mm column; solvent A, $H_2O$-0.02% TFA; solvent B, MeCN-0.02% TFA; flow rate: 2 mL/min; start 2% B, final 98% B in 4 min, linear gradient. Method 2: Waters 2795 pump and Waters 2996 photodiode array detector set at 214 nm with the MS detection performed with a Waters ZQ mass spectrometer (ESI); Epic Polar Hydrophilic 3 μm, 120 Å, 3.2×30 mm column; solvent A, $H_2O$-0.03% $HCO_2H$; solvent B, MeCN-0.03% $HCO_2H$; flow rate) 2 mL/min; start 10% B, final 100% B in 3 min linear gradient, remaining for 1 min. Unless otherwise noted, compounds were purified using either of the following methods. Flash column chromatography was performed on EM Science silica gel 60 (particle size of 32-63 μm, 60 Å) or commercially available silica gel column cartridges from Biotage, ISCO or Analogix. Preparative reverse-phase high-pressure liquid chromatography (RP HPLC) was performed using one of the following systems: (A) a Waters Delta prep 4000 pump/controller, a 486 detector set at 215 nm, and a LKB Ultrorac fraction collector; or (B) a Sciex LC/MS system with a 150 EX single quad mass spec, a Shimadzu LC system, a LEAP autoinjector, and a Gilson fraction collector. The sample was dissolved in a mixture of acetonitrile/20 mM aqueous ammonium acetate or acetonitrile/water/TFA, applied on a Pursuit C-18 20×100 mm column and eluted at 20 ml/min with a linear gradient of 10%-90% B, where (A): 20 mM aqueous ammonium acetate (pH 7.0) and (B): acetonitrile or (A): water with 0.05% TFA and (B): acetonitrile with 0.05% TFA. The pooled fractions were concentrated under reduced pressure and lyophilized to afford the desired compounds. $^1H$ NMR spectra were recorded using a Varian Mercury 300 MHz or Varian Inova 400 MHz spectrometer. All peak listings for the NMR data were generated using ACD Labs 1D NMR Processor version 12.0. The chemical shifts are in parts per million (δ) referenced to DMSO-d5 (2.49 ppm) or $CHCl_3$ (7.26 ppm). High-resolution mass spectra (HRMS) were recorded on a Bruker Apex II FTICR mass spectrometers with a 4.7 T magnet (ES) or Micromass AutoSpec (EI) mass spectrometers. Optical rotations were measured on a Schmidt & Haensch electronic polarimeter. The wavelength was set at 589.45 nm which is the sodium D line. Temperature was ambient room temperature. Final compounds and intermediates were named using the Auto Nom2000 feature in the MDL ISIS Draw application.

Example 1

(S)-3-Cyclopentyl-N-(1-methyl-1H-pyrazol-3-yl)-2-(1-oxo-4-trifluoromethyl-1,3-dihydro-isoindol-2-yl)-propionamide

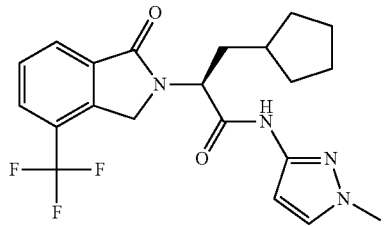 [SMILES: Cn1ccc(NC(=O)[C@H](CC2CCCC2)N2Cc3c(cccc3C(F)(F)F)C2=O)n1]

To a solution of 2-methyl-3-trifluoromethyl-benzoic acid (Apollo, 1 g, 4.90 mmol) in methanol (20 mL) was added concentrated sulfuric acid (0.5 mL) and the resulting mixture was heated to reflux overnight. The cooled reaction mixture was concentrated and diluted with water (25 mL) and a saturated sodium bicarbonate solution (25 mL). The mixture was extracted with ethyl acetate (50 mL), the organic phases combined, washed with water and dried over magnesium sulfate. The mixture was filtered and evaporated to give 2-methyl-3-trifluoromethyl-benzoic acid methyl ester (0.95 g, 4.35 mmol, 89%); $^1H$ NMR (300 MHz, $CDCl_3$) δ ppm 2.65 (s, 3H), 3.94 (s, 3H), 7.35 (t, J=7.85 Hz, 1H), 7.72-8.01 (m, 2H).

To a solution of 2-methyl-3-trifluoromethyl-benzoic acid methyl ester (0.95 g, 4.35 mmol) in benzene (10 mL) was added N-bromosuccinimide (0.77 g, 4.33 g) and benzoyl peroxide (0.052 g, 0.21 mmol) and the resulting mixture heated to reflux for 4 h, cooled and stirred at room temperature for 48 h. The mixture was filtered, the filter cake washed with diethyl ether and the filtrate washed with a 1 N sodium thiosulfate solution (10 mL), brine and dried over magnesium sulfate. The mixture was filtered and evaporated and the residue purified via automated flash chromatography (Analogix, SF25-80 g column, 5->10% ethyl acetate/hexane gradient) to give 2-bromomethyl-3-trifluoromethyl-benzoic acid methyl ester (1.04 g, 3.50 mmol, 81%) as an off white solid; $^1$H NMR (300 MHz, DMSO-$d_6$) δ ppm 3.72-4.16 (m, 3H), 5.03 (s, 2H), 7.47-8.32 (m, 3H).

(S)-2-Amino-3-cyclopentyl-propionic acid (Chemimpex, 1.0 g, 6.36 mmol), methanol (15 mL) and concentrated hydrochloric acid (2 mL) was placed in a reaction flask and heated at 65° C. for 16 h. After such time, the reaction mixture was concentrated in vacuo and then dissolved in water. The resulting solution was then treated with a saturated aqueous sodium bicarbonate solution until pH ~7-9. It was then extracted with ethyl acetate and the organic layers combined, dried over magnesium sulfate, filtered to remove the drying agent and the filtrate concentrated in vacuo to afford (S)-2-amino-3-cyclopentyl-propionic acid methyl ester (796 mg, 73%) as a clear colorless oil: HR-ES(+) m/e calcd for $C_9H_{17}NO_2$ [M+H]$^+$ 172.1332, observed 172.1332; $^1$H NMR (300 MHz, DMSO-d6) δ ppm 3.60 (s, 3H), 3.25 (dd, J=6.04, 7.85 Hz, 1H), 1.34-1.96 (m, 9H), 0.92-1.14 (m, 2H).

A mixture of 2-bromomethyl-3-trifluoromethyl-benzoic acid methyl ester (695 mg, 2.34 mmol), (S)-2-amino-3-cyclopentyl-propionic acid methyl ester (400 mg, 2.34 mmol), triethylamine (358 μL, 2.57 mmol), and acetonitrile (20 mL) was heated at 82° C. for 7 h. The crude reaction mixture was treated with water (5 mL) and then concentrated in vacuo to remove the acetonitrile. The remaining solution was then diluted with water (10 mL) and extracted with ethyl acetate (3×20 mL), the combined organics were then dried over magnesium sulfate, filtered to remove the drying agent and the filtrate concentrated in vacuo. The residue was then purified via automated flash chromatography (12 g silica gel column, 10-40% ethyl acetate/hexanes) to afford (S)-3-cyclopentyl-2-(1-oxo-4-trifluoromethyl-1,3-dihydro-isoindol-2-yl)-propionic acid methyl ester (675 mg, 81%) as a clear colorless oil: $[\alpha]^{25}{}_D$=−16.0°, (c=0.15, methylene chloride); HR-ES(+) m/e calcd for $C_{18}H_{20}NO_3F_3$ [M+H]$^+$ 356.1468, observed 356.1466; $^1$H NMR (300 MHz, DMSO-d6, ppm) δ 8.02 (t, J=8.00 Hz, 2H), 7.71-7.89 (m, 1H), 4.92 (dd, J=4.08, 10.41 Hz, 1H), 4.69 (s, 2H), 3.66 (s, 3H), 0.94-2.21 (m, 11H).

A solution (S)-3-cyclopentyl-2-(1-oxo-4-trifluoromethyl-1,3-dihydro-isoindol-2-yl)-propionic acid methyl ester (350 mg, 0.98 mmol) in tetrahydrofuran (5 mL) at room temperature was treated with a solution of lithium hydroxide monohydrate (82 mg, 1.96 mmol) in water (5 mL). The reaction mixture was then stirred at room temperature for 1 h. The reaction mixture was then acidified to pH=2 with a 1 N aqueous hydrochloric acid solution and extracted with ethyl acetate (3×20 mL). The combined organic layers were then dried over magnesium sulfate, filtered to remove the drying agent, and the filtrate concentrated in vacuo to afford (S)-3-cyclopentyl-2-(1-oxo-4-trifluoromethyl-1,3-dihydro-isoindol-2-yl)-propionic acid (293 mg, 88%) as a colorless oil: $[\alpha]^{28}{}_D$=−5.3° (c=0.19, methylene chloride); HR-ES(+) m/e calcd for $C_{17}H_{18}NO_3F_3$ [M+H]$^+$ 342.1312, observed 342.1310; $^1$H NMR (300 MHz, DMSO-d6) δ ppm 13.13 (br. s., 1H), 8.02 (t, J=8.15 Hz, 2H), 7.68-7.85 (m, 1H), 4.82 (dd, J=4.23, 11.17 Hz, 1H), 4.69 (s, 2H), 1.02-2.20 (m, 11H).

A solution of (S)-3-cyclopentyl-2-(1-oxo-4-trifluoromethyl-1,3-dihydro-isoindol-2-yl)-propionic acid (100 mg, 0.29 mmol) in methylene chloride (2.9 mL) at 0° C. was treated with oxalyl chloride (0.03 mL, 0.34 mmol) followed by N,N-dimethylformamide (5 drops). The resulting solution was stirred at 0° C. for 30 min. At this time, the solution was warmed to room temperature and stirred for 30 min. The reaction was then concentrated in vacuo. The residue was re-suspended in methylene chloride (2×5 mL) and then concentrated in vacuo. The residue was then dissolved in methylene chloride (1 mL) and was added to a pre-cooled solution of 1-methyl-1H-pyrazol-3-ylamine (Matrix, 30 mg, 1.05 mmol) and 2,6-lutidine (0.05 mL, 0.47 mmol) in methylene chloride (3 mL) at 0° C. The reaction was allowed to gradually warm to room temperature and was stirred at room temperature overnight. After this time, the reaction was diluted with methylene chloride (50 mL) and was washed with a 1N aqueous hydrochloric acid solution (2×100 mL), a saturated aqueous sodium bicarbonate solution (2×100 mL) and water (1×100 mL), dried over sodium sulfate, filtered and concentrated in vacuo. Flash chromatography (50-75% ethyl acetate/hexanes) afforded (5)-3-cyclopentyl-N-(1-methyl-1H-pyrazol-3-yl)-2-(1-oxo-4-trifluoromethyl-1,3-dihydro-isoindol-2-yl)-propionamide (94 mg, 77%) as a white solid; ES$^-$-HRMS m/e calcd for $C_{21}H_{23}N_4O_2F_3$ (M+H)$^+$ 421.1846 found 421.1844. $^1$H-NMR (300 MHz, DMSO-$d_6$) δ ppm 10.87 (s, 1H), 8.01 (t, J=8.6 Hz, 2H), 7.68-7.81 (m, 1H), 7.54 (d, J=1.9 Hz, 1H), 6.39 (d, J=1.9 Hz, 1H), 5.02-5.15 (m, 1H), 5.03 (d, J=18.5 Hz, 1H), 4.71 (d, J=18.5 Hz, 1H), 3.73 (s, 3H), 0.98-2.12 (m, 11H).

Example 2

(S)-3-Cyclopentyl-N-[1-(2-hydroxy-ethyl)-1H-pyrazol-3-yl]-2-(1-oxo-4-trifluoromethyl-1,3-dihydro-isoindol-2-yl)-propionamide

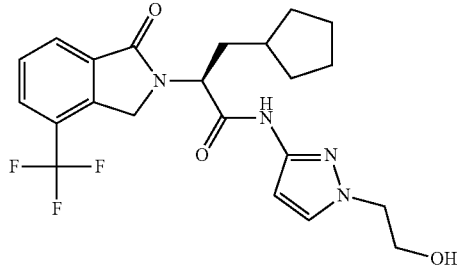 [SMILES: O=C(Nc1ccn(CCO)n1)[C@H](CC1CCCC1)N1Cc2c(cccc2C(F)(F)F)C1=O]

A solution of 1-[2-(tert-butyl-dimethyl-silanyloxy)-ethyl]-3-nitro-1H-pyrazole (prepared as in US 20080021032 Example 67, 6.34 g, 23.36 mmol) in ethanol (100 mL) was treated with concentrated hydrochloric acid (12 drops) and stirred for 1 h at room temperature. After this time, another portion of concentrated hydrochloric acid was added (12 drops) and it was stirred overnight at room temperature. After this time, the reaction mixture was concentrated in vacuo and then azeotroped with acetonitrile. The crude material was then purified by flash column chromatography (silica gel 60, 230-400 mesh, 80% ethyl acetate/hexanes) to afford 2-(3-nitro-pyrazol-1-yl)-ethanol (2.36 g, 94%) as a white solid: $^1$H NMR (300 MHz, DMSO-$d_6$) δ ppm 8.00 (d, J=2.56 Hz, 1H), 7.03 (d, J=2.56 Hz, 1H), 5.00 (t, J=5.31 Hz, 1H), 4.26 (t, J=5.31 Hz, 2H), 3.77 (q, J=5.49 Hz, 2H).

A solution 2-(3-nitro-pyrazol-1-yl)-ethanol (3.46 g, 22.02 mmol) in ethanol (40 mL) was placed in a Parr shaker bottle and treated with 10% palladium on carbon (350 mg). The bottle was then put on the Parr shaker and charged with hydrogen to 50 psi and let shake for 1 h. After this time, the reaction mixture was filtered through celite and the celite washed with ethanol. The filtrate was then concentrated in vacuo and azeotroped with acetonitrile and then chloroform to afford 2-(3-amino-pyrazol-1-yl)-ethanol (3.02 g, >quant.) as a light yellow viscous oil: $^1$H NMR (300 MHz, DMSO-$d_6$ δ ppm 7.26 (d, J=1.83 Hz, 1H), 5.34 (d, J=2.20 Hz, 1H), 4.76 (t, J=5.31 Hz, 1H), 4.50 (s, 2H), 3.78-3.88 (m, 2H), 3.62 (q, J=5.74 Hz, 2H).

A solution of (S)-3-cyclopentyl-2-(1-oxo-4-trifluoromethyl-1,3-dihydro-isoindol-2-yl)-propionic acid (50 mg, 0.15 mmol, prepared as in Example 1) in methylene chloride (5 mL) and N,N-dimethylformamide (1 drop) cooled to 0° C. was treated with a solution of oxalyl chloride in methylene chloride (2.0 M, 88 μL, 0.18 mmol) and stirred at 0° C. for 10 min. After this time, the reaction mixture was warmed to room temperature and then stirred for another 25 min. After this time, the reaction mixture was then concentrated in vacuo and the residue taken up in methylene chloride (2 mL) and added dropwise to a separate reaction flask containing a mixture of 2-(3-amino-pyrazol-1-yl)-ethanol (28 mg, 0.22 mmol) and 2,6-lutidine (32 μL, 0.29 mmol) in methylene chloride (5 mL) cooled to 0° C. The resulting reaction mixture was then allowed to warm to room temperature and stirred for 16 h. After such time, the reaction mixture was quenched with a saturated aqueous sodium bicarbonate solution (10 mL) and then extracted with methylene chloride (3×15 mL). The organic layers were then washed with a 1N aqueous hydrochloric acid solution (10 mL), dried over magnesium sulfate, filtered to remove the drying agent, and the filtrate concentrated in vacuo. The crude material was purified via automated flash chromatography (4 g silica gel column, 60-95% ethyl acetate/hexanes) to afford (S)-3-cyclopentyl-N-[1-(2-hydroxy-ethyl)-1H-pyrazol-3-yl]-2-(1-oxo-4-trifluoromethyl-1,3-dihydro-isoindol-2-yl)-propionamide (57 mg, 86%) as a white foam: $[\alpha]^{29}_D=-28.5°$, (c=0.26, methylene chloride); HR-ES(+) m/e calcd for $C_{22}H_{25}N_4O_3F_3$ [M+H]$^+$ 451.1952, observed 451.1950; $^1$H NMR (300 MHz, DMSO-$d_6$) δ ppm 10.91 (s, 1H), 8.01 (t, J=8.50 Hz, 2H), 7.69-7.81 (m, 1H), 7.56 (d, J=2.27 Hz, 1H), 6.40 (d, J=2.27 Hz, 1H), 4.97-5.13 (m, 2H), 4.85 (t, J=5.29 Hz, 1H), 4.71 (d, J=18.51 Hz, 1H), 4.02 (t, J=5.67 Hz, 2H), 3.69 (q, J=5.67 Hz, 2H), 0.99-2.12 (m, 11H).

Example 3

{3-[(S)-3-Cyclopentyl-2-(1-oxo-4-trifluoromethyl-1,3-dihydro-isoindol-2-yl)-propionylamino]-pyrazol-1-yl}-acetic acid tert-butyl ester

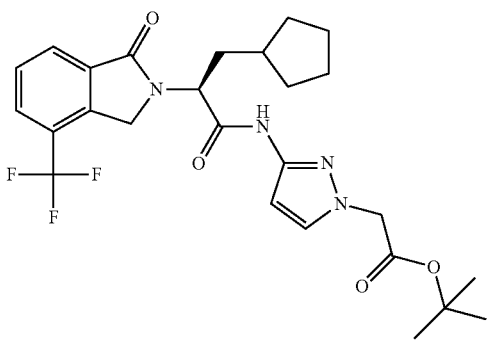 [SMILES: CC(C)(C)OC(=O)Cn1ccc(NC(=O)[C@H](CC2CCCC2)N2Cc3c(cccc3C(F)(F)F)C2=O)n1]

A solution of (S)-3-cyclopentyl-2-(1-oxo-4-trifluoromethyl-1,3-dihydro-isoindol-2-yl)-propionic acid (100 mg, 0.29 mmol, prepared as in Example 1) in methylene chloride (4 mL) and N,N-dimethylformamide (4 drops) was treated with a solution of oxalyl chloride in methylene chloride (2.0 M, 150 μL, 0.30 mmol) and stirred for 15 min at room temperature. After this time, the reaction mixture was then concentrated in vacuo and the resulting residue was dissolved in methylene chloride (4 mL) and then added dropwise to a separate reaction flask containing a mixture of (3-amino-pyrazol-1-yl)-acetic acid tert-butyl ester (prepared as in US 20080021032, Example 3, 86 mg, 0.44 mmol) and 2,6-lutidine (100 μL, 0.87 mmol) in methylene chloride (3 mL) at room temperature. The resulting reaction mixture was then stirred at room temperature for 2 h. The reaction mixture was then quenched by the addition of methanol and then diluted with methylene chloride. The organic layer was then concentrated in vacuo with silica gel (2.0 g). The silica gel with absorbed material was placed in a SIM and purified via Biotage flash column chromatography (40 S silica gel column, 25% ethyl acetate/hexanes) to afford {3-[(S)-3-cyclopentyl-2-(1-oxo-4-trifluoromethyl-1,3-dihydro-isoindol-2-yl)-propionylamino]-pyrazol-1-yl}-acetic acid tert-butyl ester (151 mg, 100%) as a white foam: HR-ES(+) m/e calcd for $C_{26}H_{31}N_4O_4F_3$ [M+H]$^+$ 521.2370, observed 521.2368; $^1$H NMR (400 MHz, CHLOROFORM-d) δ ppm 8.49 (s, 1H), 8.08 (d, J=7.46 Hz, 1H), 7.81 (d, J=7.67 Hz, 1H), 7.63 (t, J=7.67 Hz, 1H), 7.33 (d, J=2.34 Hz, 1H), 6.73 (d, J=2.34 Hz, 1H), 5.02 (dd, J=7.03, 8.52 Hz, 1H), 4.70-4.81 (m, 1H), 4.53-4.69 (m, 3H), 1.10-2.25 (m, 20H).

Example 4

{3-[(S)-3-Cyclopentyl-2-(1-oxo-4-trifluoromethyl-1,3-dihydro-isoindol-2-yl)-propionylamino]-pyrazol-1-yl}-acetic acid

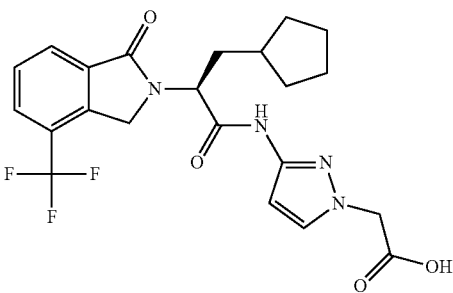 [SMILES: O=C(O)Cn1ccc(NC(=O)[C@H](CC2CCCC2)N2Cc3c(cccc3C(F)(F)F)C2=O)n1]

A mixture of {3-[(S)-3-cyclopentyl-2-(1-oxo-4-trifluoromethyl-1,3-dihydro-isoindol-2-yl)-propionylamino]-pyrazol-1-yl}-acetic acid tert-butyl ester (133 mg, 0.26 mmol, prepared as in Example 3) and lithium hydroxide monohydrate (22 mg, 0.52 mmol) in tetrahydrofuran:water (1:1, 10 mL) at room temperature was stirred for 2 h. The reaction mixture was then concentrated in vacuo and partitioned between a 1 N aqueous hydrochloric acid solution and ethyl acetate. The organic layer was then dried over magnesium sulfate, filtered to remove the drying agent, and the filtrate concentrated in vacuo to afford {3-[(S)-3-cyclopentyl-2-(1-oxo-4-trifluoromethyl-1,3-dihydro-isoindol-2-yl)-propionylamino]-pyrazol-1-yl}-acetic acid (118 mg, 98%) as a white foam: HR-ES(+) m/e calcd for $C_{22}H_{23}N_4O_4F_3$ [M+H]$^+$ 465.1744, observed 465.1744; $^1$H NMR (400 MHz, DMSO-d6) δ ppm 10.93 (s, 1H), 8.01 (dd, J=7.67, 13.00 Hz, 2H), 7.69-7.80 (m, 1H), 7.59 (d, J=2.13 Hz, 1H), 6.45 (d, J=2.13 Hz, 1H), 4.95-5.12 (m, 2H), 4.81 (s, 2H), 4.72 (d, J=17.90 Hz, 1H), 1.09-2.11 (m, 11H).

Example 5

(S)-3-Cyclopentyl-N-[1-((R)-2,3-dihydroxy-propyl)-1H-pyrazol-3-yl]-2-(1-oxo-4-trifluoromethyl-1,3-dihydro-isoindol-2-yl)-propionamide

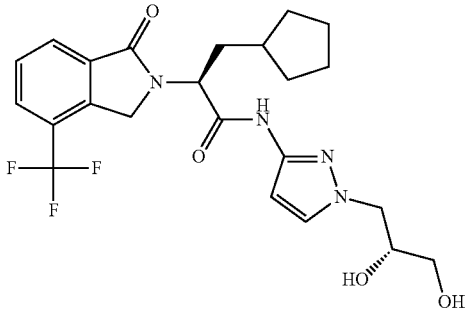 [SMILES: O=C(Nc1ccn(C[C@@H](O)CO)n1)[C@H](CC1CCCC1)N1Cc2c(cccc2C(F)(F)F)C1=O]

A solution of (S)-3-cyclopentyl-2-(1-oxo-4-trifluoromethyl-1,3-dihydro-isoindol-2-yl)-propionic acid (100 mg, 0.29 mmol, prepared as in Example 1) in methylene chloride (5 mL) and N,N-dimethylformamide (5 drops) was treated with a solution of oxalyl chloride in methylene chloride (2.0 M, 200 μL, 0.40 mmol) and stirred for 15 min at room temperature. After this time, the reaction mixture was then concentrated in vacuo and the resulting residue was dissolved in methylene chloride (5 mL) and then added dropwise to a separate reaction flask containing a mixture of (R)-3-(3-amino-pyrazol-1-yl)-propane-1,2-diol (prepared as in US 20080021032, Example 35, 70 mg, 0.45 mmol) and 2,6-lutidine (250 μL) in methylene chloride (3 mL) at room temperature. The resulting reaction mixture was then stirred at room temperature for 2 h. The reaction mixture was quenched by the addition of methanol and then diluted with methylene chloride. The organic layer was then washed with a 1 N aqueous hydrochloric acid solution. The organic layer was then concentrated in vacuo with silica gel (2.0 g). The silica gel with absorbed material was placed in a SIM and purified via Biotage flash column chromatography (40 S silica gel column, 100% ethyl acetate to 10% methanol/ethyl acetate) to afford (S)-3-cyclopentyl-N-[1-((R)-2,3-dihydroxy-propyl)-1H-pyrazol-3-yl]-2-(1-oxo-4-trifluoromethyl-1,3-dihydro-isoindol-2-yl)-propionamide (98 mg, 69%) as a white foam: $[\alpha]^{29}_D$=+12.0°, (c=0.15, methanol); HR-ES(+) m/e calcd for $C_{23}H_{27}N_4O_4F_3$ [M+H]$^+$ 481.2057, observed 481.2055; $^1$H NMR (400 MHz, DMSO-d6) δ ppm 10.91 (s, 1H), 7.94-8.05 (m, 2H), 7.71-7.79 (m, 1H), 7.53 (d, J=2.34 Hz, 1H), 6.40 (d, J=2.13 Hz, 1H), 4.99-5.11 (m, 2H), 4.93 (d, J=5.33 Hz, 1H), 4.67-4.76 (m, 2H), 4.09 (dd, J=3.84, 13.85 Hz, 1H), 3.81-3.91 (m, 1H), 3.76 (br. s., 1H), 3.23-3.31 (m, 2H), 1.05-2.13 (m, 11H).

Example 6

(S)-3-Cyclopentyl-N-[1-((S)-2,3-dihydroxy-propyl)-1H-pyrazol-3-yl]-2-(1-oxo-4-trifluoromethyl-1,3-dihydro-isoindol-2-yl)-propionamide

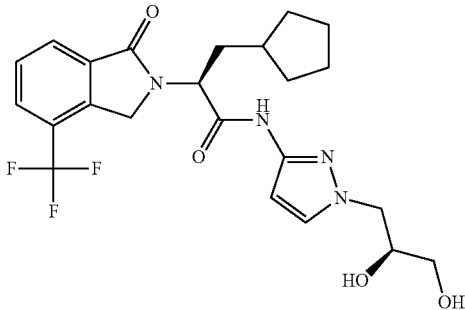 [SMILES: O=C(Nc1ccn(C[C@H](O)CO)n1)[C@H](CC1CCCC1)N1Cc2c(cccc2C(F)(F)F)C1=O]

A solution of (S)-3-cyclopentyl-2-(1-oxo-4-trifluoromethyl-1,3-dihydro-isoindol-2-yl)-propionic acid (100 mg, 0.29 mmol, prepared as in Example 1) in methylene chloride (5 mL) and N,N-dimethylformamide (5 drops) was treated with a solution of oxalyl chloride in methylene chloride (2.0 M, 200 μL, 0.40 mmol) and stirred for 15 min at room temperature. After this time, the reaction mixture was then concentrated in vacuo and the resulting residue was dissolved in methylene chloride (5 mL) and then added dropwise to a separate reaction flask containing a mixture of (S)-3-(3-amino-pyrazol-1-yl)-propane-1,2-diol (prepared as in US 20080021032, Example 34, 70 mg, 0.45 mmol) and 2,6-lutidine (250 μL) in methylene chloride (3 mL) at room temperature. The resulting reaction mixture was then stirred at room temperature for 2 h. The reaction mixture was quenched by the addition of methanol and then diluted with methylene chloride. The organic layer was then washed with a 1 N aqueous hydrochloric acid solution. The organic layer was then concentrated in vacuo with silica gel (2.0 g). The silica gel with absorbed material was placed in a SIM and purified via Biotage flash column chromatography (40 S silica gel column, 100% ethyl acetate to 5% methanol/ethyl acetate) to afford (S)-3-cyclopentyl-N-[1-((S)-2,3-dihydroxy-propyl)-1H-pyrazol-3-yl]-2-(1-oxo-4-trifluoromethyl-1,3-dihydro-isoindol-2-yl)-propionamide (99 mg, 69%) as a white foam: $[\alpha]^{28}_D$=−12.0°, (c=0.15, methanol); HR-ES(+) m/e calcd for $C_{23}H_{27}N_4O_4F_3$ [M+H]$^+$ 481.2057, observed 481.2057; $^1$H NMR (400 MHz, DMSO-d6) δ ppm 10.92 (s, 1H), 7.94-8.05 (m, 2H), 7.73-7.80 (m, 1H), 7.53 (d, J=2.13 Hz, 1H), 6.40 (d, J=2.13 Hz, 1H), 4.98-5.11 (m, 2H), 4.93 (d, J=5.33 Hz, 1H), 4.67-4.75 (m, 2H), 4.09 (dd, J=4.05, 13.64 Hz, 1H), 3.81-3.91 (m, 1H), 3.77 (br. s., 1H), 3.24-3.30 (m, 2H), 1.99-2.09 (m, 1H), 1.06-1.95 (m, 10H).

Example 7

(S)-3-Cyclopentyl-N-[1-(2-methoxy-2-methyl-propyl)-1H-pyrazol-3-yl]-2-(1-oxo-4-trifluoromethyl-1,3-dihydro-isoindol-2-yl)-propionamide

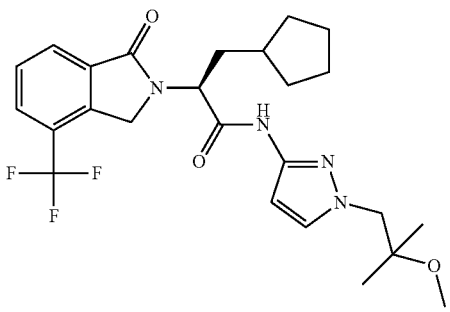 [SMILES: COC(C)(C)Cn1ccc(NC(=O)[C@H](CC2CCCC2)N2Cc3c(cccc3C(F)(F)F)C2=O)n1]

A solution of (S)-3-cyclopentyl-2-(1-oxo-4-trifluoromethyl-1,3-dihydro-isoindol-2-yl)-propionic acid (50 mg, 0.15 mmol, prepared as in Example 1) in methylene chloride (5 mL) and N,N-dimethylformamide (1 drop) cooled to 0° C. was treated with a solution of oxalyl chloride in methylene chloride (2.0 M, 88 μL, 0.18 mmol) and stirred at 0° C. for 10 min. After this time, the reaction mixture was warmed to room temperature and then stirred for another 25 min. After this time, the reaction mixture was then concentrated in vacuo and the residue taken up in methylene chloride (2 mL) and added dropwise to a separate reaction flask containing a mixture of 1-(2-methoxy-2-methyl-propyl)-1H-pyrazol-3-ylamine (prepared as in US 20080021032, Example 94, 37 mg, 0.22 mmol) and 2,6-lutidine (32 μL, 0.29 mmol) in methylene chloride (5 mL) cooled to 0° C. The resulting reaction mixture was then allowed to warm to room temperature and stirred for 16 h. After such time, the reaction mixture was quenched with a saturated aqueous sodium bicarbonate solution (10 mL) and then extracted with methylene chloride (3×15 mL). The organic layers were then washed with a 1N aqueous hydrochloric acid solution (10 mL), dried over magnesium sulfate, filtered to remove the drying agent, and the filtrate concentrated in vacuo. The crude material was purified via automated flash chromatography (4 g silica gel column, 50% ethyl acetate/hexanes) to afford (S)-3-cyclopentyl-N-[1-(2-methoxy-2-methyl-propyl)-1H-pyrazol-3-yl]-2-(1-oxo-4-trifluoromethyl-1,3-dihydro-isoindol-2-yl)-propionamide (51 mg, 71%) as a white foam: $[\alpha]^{32}_D$=−41.1°, (c=0.09, methylene chloride); HR-ES(+) m/e calcd for $C_{25}H_{31}N_4O_3F_3$ [M+H]$^+$ 493.2421, observed 493.2419; $^1$H NMR (300 MHz, DMSO-d6) δ ppm 10.95 (s, 1H), 8.01 (t, J=8.60 Hz, 2H), 7.68-7.81 (m, 1H), 7.49 (d, J=1.81 Hz, 1H), 6.44 (d, J=2.11 Hz, 1H), 4.97-5.17 (m, 2H), 4.71 (d, J=18.41 Hz, 1H), 3.92-4.08 (m, 2H), 3.06-3.22 (m, 3H), 0.93-2.16 (m, 17H).

Example 8

(S)-3-Cyclohexyl-N-[1-(2-methoxy-ethyl)-1H-pyrazol-3-yl]-2-(1-oxo-1,3-dihydro-isoindol-2-yl)-propionamide

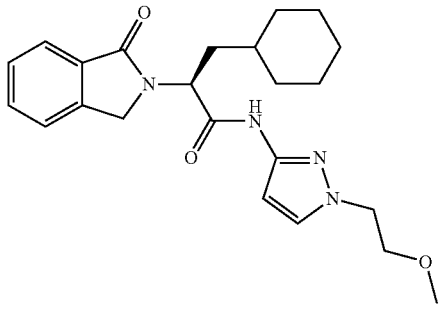 [SMILES: COCCn1ccc(NC(=O)[C@H](CC2CCCCC2)N2Cc3ccccc3C2=O)n1]

A mixture of (S)-(+)-α-aminocyclohexanepropionic acid hydrate (5.00 g, 29.2 mmol) and phthalic dicarboxaldehyde (4.21 g, 31.3 mmol) in acetonitrile (120 mL) was refluxed for 20 h under nitrogen. The mixture was allowed to cool to room temperature and further cooled to 0° C. The solid was filtered off and washed once with cold acetonitrile (50 mL) to afford (6.54 g, 78%) (S)-3-cyclohexyl-2-(1-oxo-1,3-dihydro-isoindol-2-yl)-propionic acid as a white solid: EI-HRMS m/e calcd for $C_{17}H_{21}NO_3$ (M$^+$) 287.1521, found 287.1521.

To a solution of (S)-3-cyclohexyl-2-(1-oxo-1,3-dihydro-isoindol-2-yl)-propionic acid (60 mg, 0.21 mmol) and 1-(2-methoxy-ethyl)-1H-pyrazol-3-ylamine (prepared as in US 20080021032, Example 72, 0.031 g, 0.22 mmol) and benzotriazole-1-yl-oxy-tris-(dimethylamino)-phosphonium hexafluorophosphate (Chemimpex, 0.11 g, 0.25 mmol) in methylene chloride (3 mL) was added N,N-diisopropylethylamine (0.11 mL, 0.63 mmol) dropwise and the resulting solution stirred at room temperature over night. The solution was diluted with methylene chloride, washed with a 1 N hydrochloric acid solution (15 mL), a saturated sodium chloride solution (20 mL) dried over magnesium sulfate. The mixture was filtered and evaporated and the resulting material purified via automated flash chromatography (Analogix, SF4-40 g column, 70-100% ethyl acetate/hexanes) to give (S)-3-cyclohexyl-N-[1-(2-methoxy-ethyl)-1H-pyrazol-3-yl]-2-(1-oxo-1,3-dihydro-isoindol-2-yl)-propionamide (31 mg, 36%) as an off white solid: $[\alpha]^{28}_D$=−69.7°, (c=0.31, chloroform); HR-ES(+) m/e calcd for $C_{23}H_{30}N_4O_3$ [M+H]$^+$ 411.2391, observed 411.2389; $^1$H NMR (300 MHz, DMSO-d$_6$) δ ppm 0.84-1.24 (m, 7H) 1.47-1.99 (m, 2H) 3.18 (s, 4H) 3.49-5.29 (m, 8H) 6.36 (s, 1H) 7.31-7.89 (m, 7H) 10.83 (s, 1H).

Example 9

(S)-3-Cyclopentyl-N-[1-(2-methoxy-ethyl)-1H-pyrazol-3-yl]-2-(1-oxo-1,3-dihydro-isoindol-2-yl)-propionamide

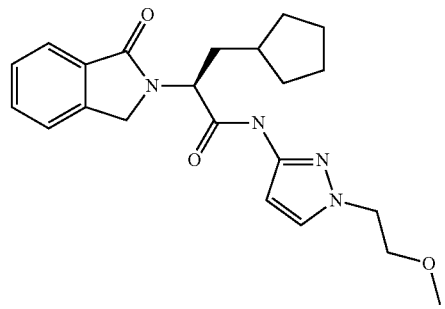 [SMILES: COCCn1ccc(NC(=O)[C@H](CC2CCCC2)N2Cc3ccccc3C2=O)n1]

A solution of benzene-1,2-dicarbaldehyde (1.9 g, 14 mmol) and (S)-2-amino-3-cyclopentyl-propionic acid (2.0 g, 13 mmol) in acetonitrile was heated to reflux for 17 h. The solution was cooled to 4° C. for 3 h during which time a precipitate formed. The mixture was filtered and the solid washed with cold acetonitrile and dried under vacuum to give (S)-3-cyclopentyl-2-(1-oxo-1,3-dihydro-isoindol-2-yl)-propionic acid (3.0 g, 86%) as a white solid: LR-ES(+) m/e calcd for $C_{16}H_{19}NO_3$ [M+H]$^+$ 274.15, observed 274.1; $^1$H NMR (300 MHz, DMSO-d$_6$) δ ppm 0.89-2.29 (m, 11H), 4.23-5.12 (m, 3H), 7.20-7.99 (m, 4H), 13.00 (s, 1H).

To a solution of (S)-3-cyclopentyl-2-(1-oxo-1,3-dihydro-isoindol-2-yl)-propionic acid (100 mg, 0.37 mmol) and 1-(2-methoxy-ethyl)-1H-pyrazol-3-ylamine (prepared as in US 20080021032, Example 72, 0.054 g, 0.38 mmol) and benzotriazole-1-yl-oxy-tris-(dimethylamino)-phosphonium hexafluorophosphate (Chemimpex, 0.19 g, 0.44 mmol) in methylene chloride (5 mL) was added N,N-diisopropylethylamine (0.19 mL, 1.1 mmol) dropwise and the resulting solution stirred at room temperature over night. The solution was diluted with methylene chloride, washed with a 1 N hydrochloric acid solution (15 mL), a saturated sodium chloride solution (20 mL) dried over magnesium sulfate. The mixture was filtered and evaporated and the resulting material purified via automated flash chromatography (Analogix, SF4-40 g column, 50-70% ethyl acetate/hexanes) to give (S)-3-cyclopentyl-N-[1-(2-methoxy-ethyl)-1H-pyrazol-3-yl]-2-(1-oxo-1,3-dihydro-isoindol-2-yl)-propionamide (94 mg, 65%) as an off white solid: $[\alpha]^{29}_D$=−62.6°, (C=0.31, chloroform); HR-ES(+) m/e calcd for $C_{22}H_{28}N_4O_3$ [M+Na]$^+$ 419.2053, observed 419.2055; $^1$H NMR (300 MHz, DMSO-d$_6$) δ ppm 1.01-2.09 (m, 7H), 3.18 (s, 4H), 3.61 (t, J=5.28 Hz, 2H), 4.12

(t, J=5.13 Hz, 2H), 4.38-5.23 (m, 4H), 6.37 (d, J=2.11 Hz, 1H), 7.32-7.84 (m, 7H), 10.84 (s, 1H).

Example 10

(S)-3-Cyclopropyl-N-[1-(2-methoxy-2-methyl-propyl)-1H-pyrazol-3-yl]-2-(1-oxo-1,3-dihydro-isoindol-2-yl)-propionamide

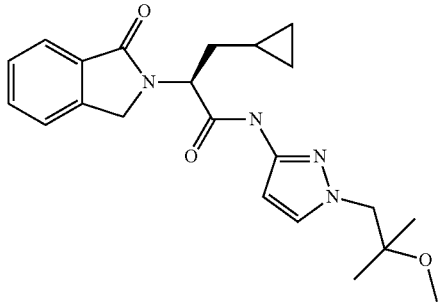 [SMILES: COC(C)(C)Cn1ccc(NC(=O)[C@H](CC2CC2)N2Cc3ccccc3C2=O)n1]

A solution of benzene-1,2-dicarbaldehyde (340 mg, 2.55 mmol) and (S)-2-amino-3-cyclopropyl-propionic acid (300 mg, 2.32 mmol) in acetonitrile (15 mL) was heated to reflux for 18 h. The solution was cooled, concentrated and the residue redissolved in methylene chloride (50 mL). The solution was extracted with a saturated sodium bicarbonate solution. The layers were separated and the aqueous phase was acidified (pH=2) with hydrochloric acid (3N), extracted with methylene chloride (2×50 mL). The organic phases were combined, dried over magnesium sulfate, filtered and evaporated to give (S)-3-cyclopropyl-2-(1-oxo-1,3-dihydro-isoindol-2-yl)-propionic (170 mg, 30%) as a yellow solid: LR-ES (+) m/e calcd for $C_{14}H_{15}NO_3$ $[M+H]^+$ 246.29, observed 246.2; $^1$H NMR (DMSO-d$_6$) δ7.24-7.94 (m, 4H), 4.83 (dd, J=10.6, 4.8 Hz, 1H), 4.54 (s, 2H), 3.16 (d, J=3.6 Hz, 1H), 1.90-2.16 (m, 1H), 1.54-1.79 (m, 1H), 0.65 (dd, J=7.8, 5.4 Hz, 1H), 0.29-0.48 (m, 2H), −0.01-0.19 (m, 2H).

To a solution of (S)-3-cyclopropyl-2-(1-oxo-1,3-dihydro-isoindol-2-yl)-propionic acid (85 mg, 0.35 mmol) and 1-(2-methoxy-2-methyl-propyl)-1H-pyrazol-3-ylamine (prepared as in US 20080021032, Example 94, 64 mg, 0.38 mmol) and benzotriazole-1-yl-oxy-tris-(dimethylamino)-phosphonium hexafluorophosphate (Chemimpex, 0.18 g, 0.42 mmol) in methylene chloride (8 mL) was added N,N-diisopropylethylamine (0.18 mL, 1.0 mmol) dropwise and the resulting solution stirred at room temperature for 4 h. The solution was diluted with methylene chloride, washed with a 1 N hydrochloric acid solution (25 mL), a saturated sodium bicarbonate solution (25 mL) dried over magnesium sulfate. The mixture was filtered and evaporated and the resulting material purified via automated flash chromatography (Analogix, SF4-40 g column, 50-70% ethyl acetate/hexanes) to give (S)-3-cyclopropyl-N-[1-(2-methoxy-2-methyl-propyl)-1H-pyrazol-3-yl]-2-(1-oxo-1,3-dihydro-isoindol-2-yl)-propionamide (46 mg, 34%) as an off white solid: $[\alpha]^{30}_D$=−38.1°, (c=0.21, chloroform); HR-ES(+) m/e calcd for $C_{22}H_{28}N_4O_3$ $[M+H]^+$ 397.2234, observed 397.2235; $^1$H NMR (300 MHz, DMSO-d$_6$) δ ppm 0.03-1.69 (m, 9H), 2.00-2.28 (m, 1H), 3.15 (s, 4H), 3.99 (s, 2H), 4.36-5.39 (m, 4H), 6.42 (d, J=1.81 Hz, 1H), 7.25-7.88 (m, 6H), 10.80 (s, 1H).

Example 11

(S)-3-Cyclopentyl-N-[1-(2-isopropoxy-ethyl)-1H-pyrazol-3-yl]-2-(1-oxo-1,3-dihydro-isoindol-2-yl)-propionamide

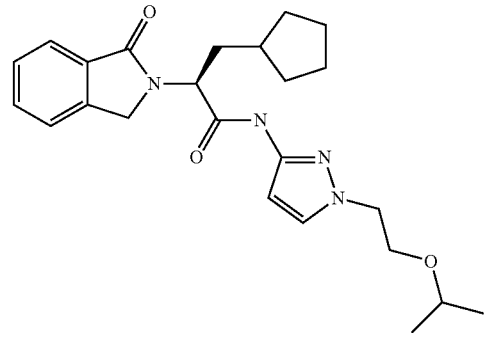 [SMILES: CC(C)OCCn1ccc(NC(=O)[C@H](CC2CCCC2)N2Cc3ccccc3C2=O)n1]

To a solution of (S)-3-cyclopentyl-2-(1-oxo-1,3-dihydro-isoindol-2-yl)-propionic acid (prepared as in Example 9, 94 mg, 0.35 mmol) and 1-(2-isopropoxy-ethyl)-1H-pyrazol-3-ylamine (prepared as in US 20080021032, Example 101, 70 mg, 0.41 mmol) and benzotriazole-1-yl-oxy-tris-(dimethylamino)-phosphonium hexafluorophosphate (Chemimpex, 0.18 g, 0.41 mmol) in methylene chloride (5 mL) was added N,N-diisopropylethylamine (0.18 mL, 1.0 mmol) dropwise and the resulting solution stirred at room temperature for 4 h. The solution was diluted with methylene chloride, washed with a 1 N hydrochloric acid solution (25 mL), a saturated sodium bicarbonate solution (25 mL) dried over magnesium sulfate. The mixture was filtered and evaporated and the resulting material purified via automated flash chromatography (Analogix, SF4-12 g column, 50% ethyl acetate/hexane) to afford (S)-3-cyclopentyl-N-[1-(2-methoxy-ethyl)-1H-pyrazol-3-yl]-2-(1-oxo-1,3-dihydro-isoindol-2-yl)-propionamide (110 mg, 75%) as an off white solid: $[\alpha]^{31}_D$=−50.6°, (c=0.36, chloroform); HR-ES(+) m/e calcd for $C_{24}H_{32}N_4O_3$ $[M+H]^+$ 425.2547, observed 425.2547; $^1$H NMR (300 MHz, DMSO-d$_6$) δ ppm 0.77-2.18 (m, 17H), 3.40-5.25 (m, 8H), 6.39 (d, J=2.11 Hz, 1H), 7.26-7.91 (m, 5H), 10.86 (s, 1H).

Example 12

(S)-3-Cyclopentyl-N-[1-(3-hydroxy-propyl)-1H-pyrazol-3-yl]-2-(1-oxo-1,3-dihydro-isoindol-2-yl)-propionamide

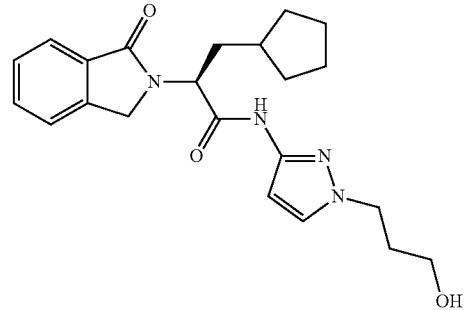 [SMILES: O=C(Nc1ccn(CCCO)n1)[C@H](CC1CCCC1)N1Cc2ccccc2C1=O]

To a solution of (S)-3-cyclopentyl-2-(1-oxo-1,3-dihydro-isoindol-2-yl)-propionic acid (prepared as in Example 9, 80 mg, 0.29 mmol) and 3-(3-amino-pyrazol-1-yl)-propan-1-ol (prepared as in US 20080021032, Example 23, 49 mg, 0.35 mmol) and benzotriazole-1-yl-oxy-tris-(dimethylamino)-phosphonium hexafluorophosphate (Chemimpex, 0.15 g, 0.35 mmol) in methylene chloride (8 mL) was added N,N-diisopropylethylamine (0.15 mL, 0.88 mmol) dropwise and the resulting solution stirred at room temperature for 4 h. The solution was diluted with methylene chloride, washed with a 1 N hydrochloric acid solution (25 mL), a saturated sodium bicarbonate solution (25 mL) dried over magnesium sulfate. The mixture was filtered and evaporated and the resulting material purified via automated flash chromatography (Analogix, SF4-12 g column, 50-70% ethyl acetate/hexanes) to afford (S)-3-cyclopentyl-N-[1-(3-hydroxy-propyl)-1H-pyrazol-3-yl]-2-(1-oxo-1,3-dihydro-isoindol-2-yl)-propionamide (28 mg, 24%) as an off white solid: HR-ES(+) m/e calcd for $C_{22}H_{28}N_4O_3$ [M+H]$^+$ 397.2234, observed 397.2233; $^1$H NMR (300 MHz, DMSO-d$_6$) δ ppm 0.94-2.34 (m, 7H), 4.04 (t, J=6.79 Hz, 3H), 4.37-5.28 (m, 6H), 6.39 (s, 2H), 7.31-7.90 (m, 8H), 10.86 (s, 2H).

Example 13

(S)-3-Cyclopentyl-N-[1-(2-methoxy-ethyl)-1H-pyrazol-3-yl]-2-(1-oxo-4-trifluoromethyl-1,3-dihydro-isoindol-2-yl)-propionamide

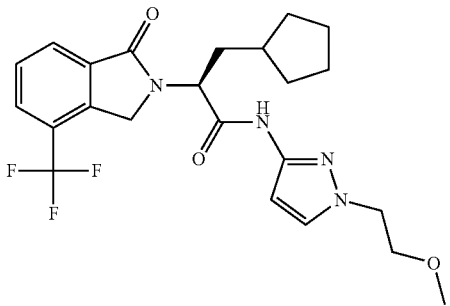 [SMILES: COCCn1ccc(NC(=O)[C@H](CC2CCCC2)N2Cc3c(cccc3C(F)(F)F)C2=O)n1]

To a solution of (S)-3-cyclopentyl-2-(1-oxo-4-trifluoromethyl-1,3-dihydro-isoindol-2-yl)-propionic acid (prepared as in Example 1, 71 mg, 0.21 mmol) and 1-(2-methoxy-ethyl)-1H-pyrazol-3-ylamine (prepared as in US 20080021032, Example 72, 32 mg, 0.23 mmol) and benzotriazole-1-yl-oxy-tris-(dimethylamino)-phosphonium hexafluorophosphate (Chemimpex, 0.11 g, 0.25 mmol) in methylene chloride (5 mL) was added N,N-diisopropylethylamine (0.11 mL, 0.62 mmol) dropwise and the resulting solution stirred at room temperature over night. The solution was diluted with methylene chloride, washed with a 1 N hydrochloric acid solution (15 mL), a saturated sodium bicarbonate solution (20 mL) dried over magnesium sulfate. The mixture was filtered and evaporated and the resulting material purified via automated flash chromatography (Analogix, SF4-12 g column, 50-80% ethyl acetate/hexanes) to give (S)-3-cyclopentyl-N-[1-(2-methoxy-ethyl)-1H-pyrazol-3-yl]-2-(1-oxo-4-trifluoromethyl-1,3-dihydro-isoindol-2-yl)-propionamide (42 mg, 43%) as an off white solid: HR-ES(+) m/e calcd for $C_{23}H_{27}N_4O_3F_3$ [M+H]$^+$ 465.2108, observed 465.2107; $^1$H NMR (300 MHz, DMSO-d$_6$) δ ppm 1.04-2.18 (m, 10H), 3.20 (s, 3H), 3.51-4.28 (m, 4H), 4.60-5.34 (m, 3H), 6.40 (d, J=1.81 Hz, 1H), 7.41-8.28 (m, 5H), 10.93 (s, 1H).

Example 14

(S)-3-Cyclopentyl-N-[1-(2-methoxy-2-methyl-propyl)-1H-pyrazol-3-yl]-2-(1-oxo-1,3-dihydro-isoindol-2-yl)-propionamide

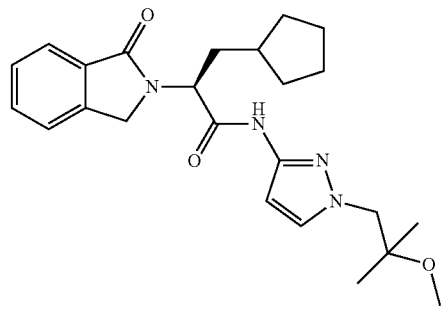 [SMILES: COC(C)(C)Cn1ccc(NC(=O)[C@H](CC2CCCC2)N2Cc3ccccc3C2=O)n1]

To a solution of (S)-3-cyclopentyl-2-(1-oxo-1,3-dihydro-isoindol-2-yl)-propionic acid (prepared as in Example 9, 0.1 g, 0.37 mmol) and 1-(2-methoxy-2-methyl-propyl)-1H-pyrazol-3-ylamine (prepared as in US 20080021032, Example 94, 0.065 g, 0.38 mmol) and benzotriazole-1-yl-oxy-tris-(dimethylamino)-phosphonium hexafluorophosphate (0.19 g, 0.44 mmol) in methylene chloride (10 mL) was added N,N-diisopropylethylamine (0.19 mL, 1.10 mmol) and the resulting solution stirred at room temperature for 19 h. The solution was diluted with methylene chloride, washed with a 1 N hydrochloric acid solution (15 mL), a saturated sodium chloride solution, and dried over magnesium sulfate. The mixture was filtered and evaporated and the resulting material purified via automated flash chromatography (Analogix, SF15-40 g column, 50%-70% ethyl acetate/hexanes) to afford (S)-3-cyclopentyl-N-[1-(2-methoxy-2-methyl-propyl)-1H-pyrazol-3-yl]-2-(1-oxo-1,3-dihydro-isoindol-2-yl)-propionamide (0.063 g, 0.21 mmol, 41%) as an off white solid; [α0]$^{29}_D$=−47.5° (c=0.28, chloroform); HR-ES(+) m/e calcd for $C_{24}H_{32}N_4O_3$ [M+Na]$^+$ 447.2366, observed 447.2368; $^1$H NMR (300 MHz, DMSO-d$_6$) δ ppm 10.88 (s, 1H), 7.70 (d, J=7.2 Hz, 1H), 7.62 (m, 2H), 7.48 (d, J=2.3 Hz, 1H), 7.45-7.54 (m, 1H), 6.43 (d, J=2.3 Hz, 1H), 5.05 (dd, J=10.7, 5.0 Hz, 1H), 4.87 (d, J=17.8 Hz, 1H), 4.53 (d, J=17.8 Hz, 1H), 3.99 (s, 2H), 3.15 (s, 3H), 1.07 (s, 3H), 1.06 (s, 3H), 0.98-2.10 (m, 11H).

Example 15

(S)-3-Cyclopentyl-2-(1-oxo-4-trifluoromethyl-1,3-dihydro-isoindol-2-yl)-N-pyrazin-2-yl-propionamide

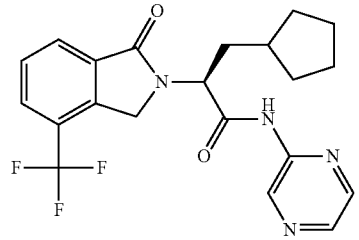 [SMILES: O=C(Nc1cnccn1)[C@H](CC1CCCC1)N1Cc2c(cccc2C(F)(F)F)C1=O]

A solution of (S)-3-cyclopentyl-2-(1-oxo-4-trifluoromethyl-1,3-dihydro-isoindol-2-yl)-propionic acid (prepared as in Example 1, 160 mg, 0.47 mmol) in methylene chloride (10 mL) and N,N-dimethylformamide (1 drop) cooled to 0° C.

was treated with a solution of oxalyl chloride in methylene chloride (2.0 M, 281 μL, 0.56 mmol) and stirred at 0° C. for 15 min. After this time, the reaction mixture was warmed to room temperature and then stirred for another 30 min. After this time, the reaction mixture was then concentrated in vacuo to ~1 mL volume and an additional amount of methylene chloride (3 mL) was added. One half of this solution of prepared acid chloride (2 mL, 0.23 mmol) was added dropwise to a separate reaction flask containing a mixture of pyrazin-2-ylamine (33 mg, 0.35 mmol) and 2,6-lutidine (52 μL, 0.47 mmol) in methylene chloride (5 mL) cooled to 0° C. The resulting reaction mixture was then allowed to warm to room temperature and stirred for 16 h. After such time, the reaction mixture was quenched with a saturated aqueous sodium bicarbonate solution (10 mL) and then extracted with methylene chloride (3×10 mL). The organic layers were then washed with a 1N aqueous hydrochloric acid solution (10 mL), dried over magnesium sulfate, filtered to remove the drying agent, and the filtrate concentrated in vacuo. The crude material was purified via automated flash chromatography (12 g silica gel column, 25-75% ethyl acetate/hexanes and then a 4 g silica gel column, 40-60% ethyl acetate/hexanes) to afford (S)-3-cyclopentyl-2-(1-oxo-4-trifluoromethyl-1,3-dihydro-isoindol-2-yl)-N-pyrazin-2-yl-propionamide (39 mg, 40%) as a white foam: $[α]^{28}_D = -65.0°$ (c=0.10, methylene chloride); HR-ES(+) m/e calcd for $C_{21}H_{21}N_4O_2F_3$ [M+H]$^+$ 419.1690, observed 416.1688; $^1$H NMR (300 MHz, DMSO-d6) δ ppm 11.32 (s, 1H), 9.26 (s, 1H), 8.34-8.49 (m, 2H), 8.02 (t, J=8.45 Hz, 2H), 7.67-7.84 (m, 1H), 5.23 (dd, J=4.98, 10.41 Hz, 1H), 5.06 (d, J=18.41 Hz, 1H), 4.67-4.85 (m, 1H), 1.02-2.21 (m, 11H).

Example 16

(S)—N-(5-Bromo-pyrazin-2-yl)-3-cyclopentyl-2-(1-oxo-4-trifluoromethyl-1,3-dihydro-isoindol-2-yl)-propionamide

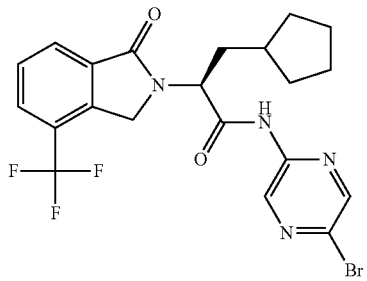 [SMILES: O=C(Nc1cnc(Br)cn1)[C@H](CC1CCCC1)N1Cc2c(cccc2C(F)(F)F)C1=O]

A solution of (S)-3-cyclopentyl-2-(1-oxo-4-trifluoromethyl-1,3-dihydro-isoindol-2-yl)-propionic acid (prepared as in Example 1, 100 mg, 0.29 mmol) in methylene chloride (4 mL) and N,N-dimethylformamide (4 drops) was treated with a solution of oxalyl chloride in methylene chloride (2.0 M, 150 μL, 0.30 mmol) and stirred for 15 min at room temperature. After this time, the reaction mixture was then concentrated in vacuo and the resulting residue was dissolved in methylene chloride (4 mL) and then added dropwise to a separate reaction flask containing a mixture of 5-bromo-pyrazin-2-ylamine (76 mg, 0.44 mmol) and 2,6-lutidine (100 μL, 0.87 mmol) in methylene chloride (3 mL) at room temperature. The resulting reaction mixture was the stirred room temperature for 1.5 h. The reaction mixture was quenched by the addition of methanol and then diluted with methylene chloride and the organic layer was washed with a 1N aqueous hydrochloric acid solution. The organic layer was then dried, filtered and the filtrate concentrated in vacuo. The crude material was purified via Biotage flash column chromatography (40 S silica gel column, 25% ethyl acetate/hexanes) to afford (S)—N-(5-bromo-pyrazin-2-yl)-3-cyclopentyl-2-(1-oxo-4-trifluoromethyl-1,3-dihydro-isoindol-2-yl)-propionamide (74 mg, 51%) as a white foam: HR-ES(+) m/e calcd for $C_{21}H_{20}N_4O_2F_3Br$ [M+H]$^+$ 497.0795, observed 497.0796; $^1$H NMR (400 MHz, DMSO-d6) δ ppm 11.50 (s, 1H), 9.09 (d, J=1.07 Hz, 1H), 8.65 (d, J=1.28 Hz, 1H), 8.02 (dd, J=7.88, 10.44 Hz, 2H), 7.77 (t, J=7.67 Hz, 1H), 5.22 (dd, J=4.90, 10.66 Hz, 1H), 5.04 (d, J=18.33 Hz, 1H), 4.76 (d, J=18.11 Hz, 1H), 1.04-2.19 (m, 11H).

Example 17

(S)-3-Cyclopentyl-N-[1-(2-isopropoy-ethyl)-1H-pyrazol-3-yl]-2-(1-oxo-4-trifluoromethyl-1,3-dihydro-isoindol-2-yl)-propionamide

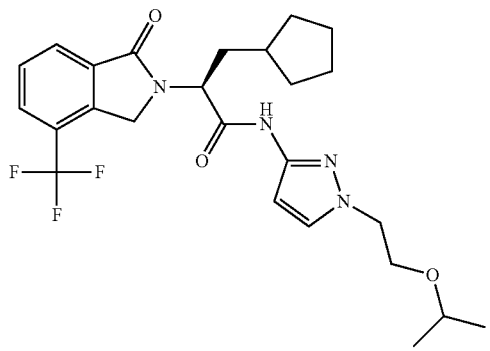 [SMILES: CC(C)OCCn1ccc(NC(=O)[C@H](CC2CCCC2)N2Cc3c(cccc3C(F)(F)F)C2=O)n1]

A solution of (S)-3-cyclopentyl-2-(1-oxo-4-trifluoromethyl-1,3-dihydro-isoindol-2-yl)-propionic acid (prepared as in Example 1, 160 mg, 0.47 mmol) in methylene chloride (10 mL) was treated with N,N-dimethylformamide (1 drop) and cooled to 0° C. It was then treated with a solution of oxalyl chloride (2.0 M in methylene chloride, 281 μL, 0.56 mmol) and stirred for 15 min at 0° C. and then warmed to room temperature and stirred for 30 min. After this time, the reaction mixture was concentrated in vacuo to about 1 mL and then methylene chloride was added (3 mL). Half of the resulting volume (~2 mL, ~0.235 mmol of the in situ generated acid chloride) was added to a flask containing 1-(2-isopropoxy-ethyl)-1H-pyrazol-3-ylamine (prepared as in US20080021032, Example 101, 60 mg, 0.35 mmol) and 2,6-lutidine (52 μL, 0.47 mmol) in methylene chloride (5 mL) at 0° C. The reaction mixture was then allowed to warm up to room temperature and stirred overnight for 16 h. After this time, the reaction mixture was quenched with an aqueous saturated sodium bicarbonate solution (10 mL) and extracted with methylene chloride (3×10 mL). The organic layers were then combined and washed with a 1N aqueous hydrochloric acid solution, dried over magnesium sulfate, filtered to remove the drying agent and the filtrate concentrated in vacuo. The crude material was purified using an Analogix Intelliflash 280 chromatography system (4 g silica gel column, 45-55% ethyl acetate/hexanes) to afford (S)-3-cyclopentyl-N-[1-(2-isopropoy-ethyl)-1H-pyrazol-3-yl]-2-(1-oxo-4-trifluoromethyl-1,3-dihydro-isoindol-2-yl)-propionamide (89 mg, 77%) as a white foam: HR-ES(+) m/e calcd for $C_{25}H_{31}N_4O_3F_3$ [M+H]$^+$493.2421, observed 493.2422; $^1$H NMR (300 MHz, DMSO-d$_6$) δ 10.93 (s, 1H), 7.89-8.19 (m, 2H), 7.68-7.83 (m, 1H), 7.56 (d, J=2.11 Hz, 1H), 6.40 (d, J=2.11 Hz, 1H), 4.91-5.25 (m, 2H), 4.71 (d, J=18.41 Hz, 1H), 4.10 (t, J=5.28 Hz, 2H), 3.57-3.79 (m, 2H), 3.47 (td, J=6.15, 12.15 Hz, 1H), 0.89-2.17 (m, 17H).

Example 18

(S)-3-Cyclohexyl-2-(4-fluoro-1-oxo-1,3-dihydro-isoindol-2-yl)-N-[1-(2-methoxy-ethyl)-1H-pyrazol-3-yl]-propionamide

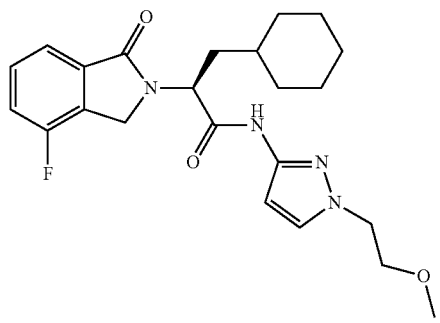 [SMILES: COCCn1ccc(NC(=O)[C@H](CC2CCCCC2)N2Cc3c(F)cccc3C2=O)n1]

A solution of 3-fluoro-2-methyl-benzoic acid (Aldrich, 10.2 g, 66.17 mmol) in methanol (135 mL) at room temperature was treated with boron trifluoride etherate (15 mL) and was allowed to stir at room temperature. The reaction mixture was then concentrated in vacuo to remove the methanol and then diethyl ether (~300 mL) was added. The solution was transferred to a separatory funnel and washed with water (200 mL) and a 5% aqueous sodium bicarbonate solution to pH>7.5. The organic layer was then dried over magnesium sulfate and concentrated in vacuo to afford 3-fluoro-2-methyl-benzoic acid methyl ester (9.74 g, 87%) as a light orange colored oil which was used without purification.

A solution of 3-fluoro-2-methyl-benzoic acid methyl ester (3.64 g, 21.67 mmol) in carbon tetrachloride (100 mL) was treated with N-bromosuccinimide (3.85 g, 21.63 mmol) and benzoyl peroxide (0.1 g). The reaction mixture was then heated at reflux temperature and after 3 h the heat was removed and it was stirred at room temperature over the weekend. The reaction was then filtered to remove the solids and concentrated in vacuo to yield a light yellow oil. The reaction was then repeated with the remaining 3-fluoro-2-methyl-benzoic acid methyl ester (6.1 g, 36.3 mmol) in carbon tetrachloride using N-bromosuccinimide (6.5 g, 36.5 mmol) and benzoyl peroxide (0.1 g) heating at reflux. The reaction mixture was then filtered and concentrated in vacuo. The two material from the two reactions was combined and purified by flash column chromatography (silica gel, 10% diethyl ether/hexanes) to afford 2-bromomethyl-3-fluoro-benzoic acid methyl ester (14.22 g, 99%) as a white solid.

A solution of (S)-2-amino-3-cyclohexyl-propionic acid methyl ester hydrochloride (Novabiochem, 500 mg, 2.25 mmol) in acetonitrile (20 mL) was placed in a flask and treated with 2-bromomethyl-3-fluoro-benzoic acid methyl ester (557 mg, 2.25 mmol) and triethylamine (660 µL, 4.74 mmol). The reaction mixture was then heated at reflux (82° C.) overnight for 16 h. After this time, the reaction mixture was diluted with water (5 mL) and concentrated in vacuo to remove the acetonitrile. The remaining material was then diluted with another portion of water (10 mL) and extracted with ethyl acetate (3×20 mL). The combined organic layers were then dried over magnesium sulfate, filtered to remove the drying agent and the filtrate concentrated in vacuo. The crude material was purified using an Analogix Intelliflash 280 chromatography system (RS-40 silica gel column, 10-25% ethyl acetate/hexanes) to afford (S)-3-cyclohexyl-2-(4-fluoro-1-oxo-1,3-dihydro-isoindol-2-yl)-propionic acid methyl ester (411 mg, 57%) as a clear colorless oil: [α]$^{30}_D$=−17.3° (c=0.30, methylene chloride); HR-ES(+) m/e calcd for $C_{18}H_{22}NO_3F$ [M+H]$^+$ 320.1657, observed 320.1656; $^1$H NMR (300 MHz, DMSO-d$_6$) δ 7.54-7.63 (m, 2H), 7.42-7.54 (m, 1H), 4.96 (dd, J=4.53, 11.47 Hz, 1H), 4.49-4.65 (m, 2H), 3.63 (s, 3H), 1.48-1.99 (m, 7H), 0.74-1.23 (m, 6H).

A mixture of (S)-3-cyclohexyl-2-(4-fluoro-1-oxo-1,3-dihydro-isoindol-2-yl)-propionic acid methyl ester (311 mg, 0.97 mmol) in tetrahydrofuran (6 mL) at room temperature was treated with a mixture of lithium hydroxide monohydrate (82 mg, 1.95 mL) in water (6 mL). The reaction mixture was then stirred at room temperature until the reaction was complete by TLC (~2 h). After this time, the reaction mixture was treated with 1N aqueous hydrochloric acid solution until the pH=2. The reaction mixture was then extracted with ethyl acetate (3×20 mL). The combined organic layers were then dried over magnesium sulfate, filtered to remove the drying agent and the filtrate was concentrated in vacuo to afford (S)-3-cyclohexyl-2-(4-fluoro-1-oxo-1,3-dihydro-isoindol-2-yl)-propionic acid (230 mg, 78%) as a white solid.

A solution of (S)-3-cyclohexyl-2-(4-fluoro-1-oxo-1,3-dihydro-isoindol-2-yl)-propionic acid (230 mg, 0.75 mmol) in methylene chloride (10 mL) was treated with N,N-dimethylformamide (1 drop) and cooled to 0° C. It was then treated with a solution of oxalyl chloride (2.0 M in methylene chloride, 452 µL, 0.91 mmol) and stirred for 15 min at 0° C. and then warmed to room temperature and stirred for 30 min. After this time, the reaction mixture was concentrated in vacuo to about 1 mL and then methylene chloride was added (5 mL). One third of the resulting volume (~2 mL, ~0.25 mmol of the in situ generated acid chloride) was added to a flask containing 1-(2-methoxy-ethyl)-1H-pyrazol-3-ylamine (prepared as in US20080021032, Example 72, 53 mg, 0.38 mmol) and 2,6-lutidine (55 µL, 0.50 mmol) in methylene chloride (5 mL) at 0° C. The reaction mixture was then allowed to warm up to room temperature and stirred overnight for 16 h. After this time, the reaction mixture was quenched with an aqueous saturated sodium bicarbonate solution (10 mL) and extracted with methylene chloride (3×10 mL). The organic layers were then combined and washed with a 1N aqueous hydrochloric acid solution, dried over magnesium sulfate, filtered to remove the drying agent and the filtrate concentrated in vacuo. The crude material was purified using an Analogix Intelliflash 280 chromatography system (4 g silica gel column, 40-60% ethyl acetate/hexanes) to afford (S)-3-cyclohexyl-2-(4-fluoro-1-oxo-1,3-dihydro-isoindol-2-yl)-N-[1-(2-methoxy-ethyl)-1H-pyrazol-3-yl]-propionamide (70 mg, 65%) as a white foam: [α]$^{28}_D$=−63.0° (c=0.10, methylene chloride); HR-ES(+) m/e calcd for $C_{23}H_{29}N_4O_3F$ [M+H]$^+$ 429.2297, observed 429.2297; $^1$H NMR (300 MHz, DMSO-d$_6$) δ 10.88 (s, 1H), 7.41-7.62 (m, 4H), 6.39 (d, J=2.11 Hz, 1H), 5.11 (dd, J=4.68, 10.72 Hz, 1H), 4.91 (d, J=17.81

Hz, 1H), 4.61 (d, J=17.81 Hz, 1H), 4.14 (t, J=4.98 Hz, 2H), 3.63 (t, J=4.98 Hz, 2H), 3.20 (s, 3H), 1.46-2.02 (m, 7H), 0.83-1.24 (m, 6H).

Example 19

3-{3-[(S)-3-Cyclopentyl-2-(1-oxo-4-trifluoromethyl-1,3-dihydro-isoindol-2-yl)-propionylamino]-pyrazol-1-yl}-propionic acid tert-butyl ester

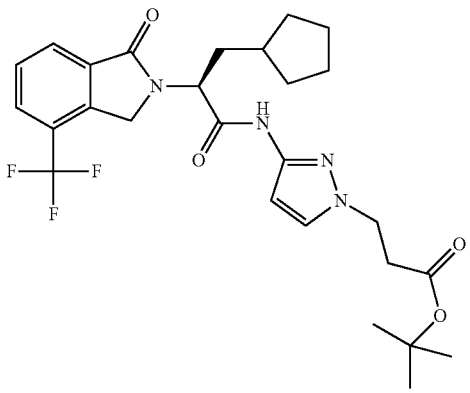 [SMILES: CC(C)(C)OC(=O)CCn1ccc(NC(=O)[C@H](CC2CCCC2)N2Cc3c(cccc3C(F)(F)F)C2=O)n1]

A solution of (S)-3-cyclopentyl-2-(1-oxo-4-trifluoromethyl-1,3-dihydro-isoindol-2-yl)-propionic acid (prepared as in Example 1, 100 mg, 0.29 mmol,) in methylene chloride (4 mL) and N,N-dimethylformamide (4 drops) was treated with a solution of oxalyl chloride in methylene chloride (2.0 M, 150 μL, 0.30 mmol) and stirred for 15 min at room temperature. After this time, the reaction mixture was then concentrated in vacuo and the resulting residue was dissolved in methylene chloride (4 mL) and then added dropwise to a separate reaction flask containing a mixture of 3-(3-amino-pyrazol-1-yl)-propionic acid tent-butyl ester (prepared as in US 20080021032, Example 8, 92 mg, 0.44 mmol) and 2,6-lutidine (100 μL, 0.87 mmol) in methylene chloride (3 mL) at room temperature. The resulting reaction mixture was the stirred room temperature for 2 h. The reaction mixture was quenched by the addition of methanol and then diluted with methylene chloride and then washed with a 1 N aqueous hydrochloric acid solution. The organic layer was then dried over sodium sulfate, filtered and the filtrate was then concentrated in vacuo with silica gel (2.0 g). The silica gel with absorbed material was placed in a SIM and purified via Biotage flash column chromatography (40 S silica gel column, 25% ethyl acetate/hexanes) to afford 3-{3-[(S)-3-cyclopentyl-2-(1-oxo-4-trifluoromethyl-1,3-dihydro-isoindol-2-yl)-propionylamino]-pyrazol-1-yl}-propionic acid tert-butyl ester (145 mg, 94%) as a white foam: HR-ES(+) m/e calcd for $C_{27}H_{33}N_4O_4F_3$ [M+H]$^+$ 535.2527, observed 535.2526; $^1$H NMR (400 MHz, DMSO-d$_6$) δ 10.91 (s, 1H), 8.01 (dd, J=7.67, 12.79 Hz, 2H), 7.71-7.82 (m, 1H), 7.56 (d, J=2.13 Hz, 1H), 6.39 (d, J=2.13 Hz, 1H), 4.96-5.14 (m, 2H), 4.71 (d, J=18.33 Hz, 1H), 4.19 (t, J=6.50 Hz, 2H), 2.72 (t, J=6.61 Hz, 2H), 0.77-2.09 (m, 20H).

Example 20

3-{3-[(S)-3-Cyclopentyl-2-(1-oxo-4-trifluoromethyl-1,3-dihydro-isoindol-2-yl)-propionylamino]-pyrazol-1-yl}-propionic acid

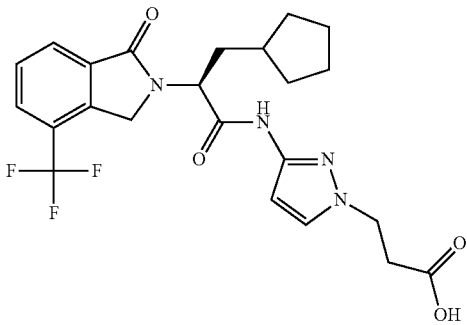 [SMILES: O=C(O)CCn1ccc(NC(=O)[C@H](CC2CCCC2)N2Cc3c(cccc3C(F)(F)F)C2=O)n1]

A mixture of 3-{3-[(S)-3-cyclopentyl-2-(1-oxo-4-trifluoromethyl-1,3-dihydro-isoindol-2-yl)-propionylamino]-pyrazol-1-yl}-propionic acid tert-butyl ester (prepared as in Example 19, 130 mg, 0.24 mmol) in methylene chloride (3 mL) at room temperature was treated with trifluoroacetic acid (1 mL) and stirred for 3 h at room temperature. The reaction mixture was then diluted with chloroform (3 mL) and washed with an aqueous semi-saturated sodium bicarbonate solution. The organic layer was then dried over magnesium sulfate, filtered to remove the drying agent, and the filtrate concentrated in vacuo to afford 3-{3-[(S)-3-cyclopentyl-2-(1-oxo-4-trifluoromethyl-1,3-dihydro-isoindol-2-yl)-propionylamino]-pyrazol-1-yl}-propionic acid (66 mg, 58%) as a white semi-solid: HR-ES(+) m/e calcd for $C_{23}H_{25}N_4O_4F_3$ [M+H]$^+$ 479.1901, observed 479.1901; $^1$H NMR (400 MHz, DMSO-d$_6$) δ 10.88 (s, 1H), 8.01 (dd, J=7.67, 15.13 Hz, 2H), 7.75 (t, J=7.56 Hz, 1H), 7.53 (d, J=2.13 Hz, 1H), 6.33 (d, J=2.13 Hz, 1H), 4.97-5.11 (m, 2H), 4.70 (d, J=18.11 Hz, 1H), 4.06 (t, J=7.46 Hz, 2H), 2.25 (t, J=7.35 Hz, 2H), 1.05-2.09 (m, 11H).

Example 21

(S)-3-Cyclopentyl-N-[5-((S)-1,2-dihydroxy-ethyl)-pyrazin-2-yl]-2-(1-oxo-4-trifluoromethyl-1,3-dihydro-isoindol-2-yl)-propionamide

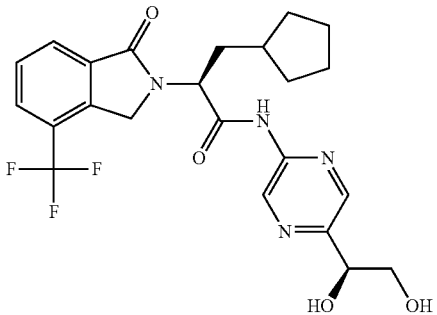 [SMILES: O=C(Nc1cnc([C@H](O)CO)cn1)[C@H](CC1CCCC1)N1Cc2c(cccc2C(F)(F)F)C1=O]

A solution of (S)-3-cyclopentyl-2-(1-oxo-4-trifluoromethyl-1,3-dihydro-isoindol-2-yl)-propionic acid (prepared as in Example 1, 125 mg, 0.37 mmol) in methylene chloride (10 mL) was treated with N,N-dimethylformamide (1 drop) and cooled to 0° C. It was then treated with a solution of oxalyl chloride (2.0 M in methylene chloride, 220 μL, 0.44 mmol) and stirred for 10 min at 0° C. and then warmed to room temperature and stirred for 30 min. After this time, the reaction mixture was concentrated in vacuo to about 1 mL and then it was added to a flask containing 5-((S)-2,2-dimethyl-[1,3]dioxolan-4-yl)-pyrazin-2-ylamine (prepared as in WO2004052869, Example 54, 107 mg, 0.55 mmol) and 2,6-lutidine (81 μL, 0.73 mmol) in methylene chloride (10 mL) at 0° C. The reaction mixture was then allowed to warm up to room temperature and stirred overnight for 16 h. After this time, the reaction mixture was quenched with an aqueous saturated sodium bicarbonate solution (10 mL) and extracted with methylene chloride (3×10 mL). The organic layers were then combined and washed with a 1N aqueous hydrochloric acid solution (10 mL), dried over magnesium sulfate, filtered to remove the drying agent and the filtrate concentrated in vacuo. The crude material was purified using an Analogix Intelliflash 280 chromatography system (12 g silica gel column, 15-40% ethyl acetate/hexanes) to afford (S)-3-cyclopentyl-N-[5-((S)-2,2-dimethyl-[1,3]dioxolan-4-yl)-pyrazin-2-yl]-2-(1-oxo-4-trifluoromethyl-1,3-dihydro-isoindol-2-yl)-propionamide (78 mg, 41%) as a white foam: $[\alpha]^{27}_D = -18.0°$ (c=0.15, methylene chloride); HR-ES(+) m/e calcd for $C_{26}H_{29}N_4O_4F_3$ $[M+Na]^+$ 541.2033, observed 541.2030; $^1H$ NMR (300 MHz, DMSO-$d_6$) δ 11.37 (s, 1H), 9.21 (d, J=1.21 Hz, 1H), 8.48 (d, J=1.21 Hz, 1H), 8.02 (t, J=8.00 Hz, 2H), 7.72-7.82 (m, 1H), 5.12-5.29 (m, 2H), 5.05 (d, J=17.81 Hz, 1H), 4.76 (d, J=18.11 Hz, 1H), 4.35 (dd, J=6.64, 8.45 Hz, 1H), 3.93 (dd, J=6.64, 8.45 Hz, 1H), 1.04-2.20 (m, 17H).

A mixture of (S)-3-cyclopentyl-N-[5-((S)-2,2-dimethyl-[1,3]dioxolan-4-yl)-pyrazin-2-yl]-2-(1-oxo-4-trifluoromethyl-1,3-dihydro-isoindol-2-yl)-propionamide (74 mg, 0.14 mmol) in tetrahydrofuran (1.5 mL) was treated with a 1N aqueous hydrochloric acid solution (1.5 mL) and stirred at room temperature until there was no more starting material as indicated by TLC (overnight, ~16 h). After this time, the reaction was treated with a saturated aqueous sodium bicarbonate solution and then extracted with ethyl acetate (3×20 mL). The organic layers were then combined and dried over magnesium sulfate, filtered to remove the drying agent and the filtrate concentrated in vacuo. The crude material was purified using an Analogix Intelliflash 280 chromatography system (4 g silica gel column, 100% ethyl acetate) to afford (S)-3-cyclopentyl-N-[5-((S)-1,2-dihydroxy-ethyl)-pyrazin-2-yl]-2-(1-oxo-4-trifluoromethyl-1,3-dihydro-isoindol-2-yl)-propionamide (49 mg, 72%) as a white foam: $[\alpha]^{28}_D = -41.6°$ (c=0.25, methylene chloride); HR-ES(+) m/e calcd for $C_{23}H_{25}N_4O_4F_3$ $[M+H]^+$ 479.1901, observed 479.1899; $^1H$ NMR (300 MHz, DMSO-$d_6$) δ 11.27 (s, 1H), 9.16 (s, 1H), 8.45 (d, J=0.91 Hz, 1H), 8.02 (t, J=8.45 Hz, 2H), 7.70-7.82 (m, 1H), 5.55 (br. s., 1H), 5.22 (dd, J=5.13, 10.26 Hz, 1H), 5.05 (d, J=18.11 Hz, 1H), 4.90-4.50 (br. s., 1H), 4.75 (d, J=18.11 Hz, 1H), 4.62 (t, J=5.13 Hz, 1H), 3.61-3.72 (m, 1H), 3.49-3.60 (m, 1H), 1.03-2.21 (m, 11H).

Example 22

(S)—N-[5-((S)-1,2-Dihydroxy-ethyl)-pyrazin-2-yl]-4-methylsulfanyl-2-(1-oxo-4-trifluoromethyl-1,3-dihydro-isoindol-2-yl)-butyramide

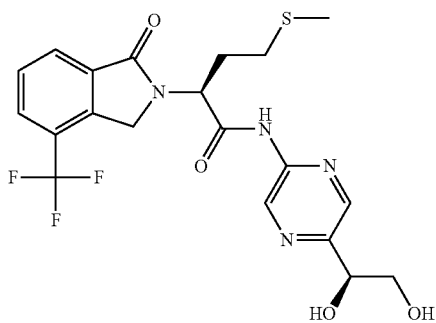 [SMILES: CSCC[C@@H](C(=O)Nc1cnc([C@H](O)CO)cn1)N1Cc2c(cccc2C(F)(F)F)C1=O]

A mixture of (S)-2-amino-4-methylsulfanyl-butyric acid methyl ester hydrochloride (Aldrich, 199 mg, 1 mmol) and 2-bromomethyl-3-trifluoromethyl-benzoic acid methyl ester (prepared as in Example 1, 297 mg, 1 mmol) in acetonitrile (5 mL) and triethylamine (280 μL, 2 mmol) was placed in a microwave reaction vessel and sealed. The reaction mixture was then placed in a microwave reactor and heated at 115° C. for 15 min. After this time, the reaction mixture was cooled and concentrated with silica gel (2 g) in vacuo. The silica gel with absorbed material was placed in a SIM and purified via Biotage flash column chromatography (40 S silica gel column, 25% ethyl acetate/hexanes) to afford (S)-4-methylsulfanyl-2-(1-oxo-4-trifluoromethyl-1,3-dihydro-isoindol-2-yl)-butyric acid methyl ester (137 mg, 40%) as a colorless viscous oil: HR-ES(+) m/e calcd for $C_{15}H_{16}NO_3SF_3$ $[M+H]^+$ 348.0876, observed 348.0874; $^1H$ NMR (400 MHz, CHLOROFORM-d) δ 8.07 (d, J=7.46 Hz, 1H), 7.83 (d, J=7.67 Hz, 1H), 7.64 (t, J=7.67 Hz, 1H), 5.25 (dd, J=4.69, 10.44 Hz, 1H), 4.79 (d, J=17.47 Hz, 1H), 4.53 (d, J=17.47 Hz, 1H), 3.77 (s, 3H), 2.38-2.62 (m, 3H), 2.16-2.31 (m, 1H), 2.13 (s, 3H).

A solution of (S)-4-methylsulfanyl-2-(1-oxo-4-trifluoromethyl-1,3-dihydro-isoindol-2-yl)-butyric acid methyl ester (134 mg, 0.39 mmol) in tetrahydrofuran/water (6 mL, 1:1) was treated with lithium hydroxide monohydrate (33 mg, 0.78 mmol) at room temperature. The reaction mixture was then stirred at room temperature for 2 h. After this time, the reaction mixture was concentrated in vacuo to remove the tetrahydrofuran. The resulting material was then diluted with a 1N aqueous hydrochloric acid solution and then extracted with ethyl acetate. The organic layers were combined and then dried over magnesium sulfate, filtered to remove the drying agent, and the filtrate was concentrated in vacuo to afford (S)-4-methylsulfanyl-2-(1-oxo-4-trifluoromethyl-1,3-dihydro-isoindol-2-yl)-butyric acid (126 mg, 97%) as a white foam: HR-ES(+) m/e calcd for $C_{14}H_{14}NO_3SF_3$ $[M+H]^+$ 334.0719, observed 334.0717; $^1H$ NMR (400 MHz, CHLOROFORM-d) δ 8.07 (d, J=7.46 Hz, 1H), 7.83 (d, J=7.67 Hz, 1H), 7.59-7.71 (m, 1H), 5.25 (dd, J=4.48, 10.44 Hz, 1H), 4.79 (d, J=17.47 Hz, 1H), 4.56 (d, J=17.47 Hz, 1H), 2.41-2.66 (m, 3H), 2.20-2.35 (m, 1H), 2.13 (s, 3H).

A solution of (S)-4-methylsulfanyl-2-(1-oxo-4-trifluoromethyl-1,3-dihydro-isoindol-2-yl)-butyric acid (57 mg, 0.17 mmol) in methylene chloride (5 mL) and N,N-dimethylformamide (3 drops) at room temperature was treated with a solution of oxalyl chloride (2.0M in methylene chloride, 210 μL, 0.34 mmol) and stirred for 15 min. After this time, the reaction mixture was concentrated in vacuo and then diluted with methylene chloride (5 mL) and added to a flask containing a solution of 5-((S)-2,2-dimethyl-[1,3]dioxolan-4-yl)-pyrazin-2-ylamine (prepared as in WO2004052869, Example 54, 67 mg, 0.34 mmol), 2,6-lutidine (64 μL, 0.34 mmol) in methylene chloride (2.5 mL) at room temperature. The reaction mixture was then stirred at room temperature for a period of 2 h. After this time, the reaction mixture was treated with methanol and then diluted with methylene chloride. The reaction mixture was then transferred to a separatory funnel and washed with a 1N aqueous hydrochloric acid solution. The organic layer was then dried over magnesium sulfate, filtered to remove the drying agent and the filtrate was concentrated with silica gel (2 g). The silica gel with absorbed material was placed in a SIM and purified via Biotage flash column chromatography (40 S silica gel column, 40%-60% ethyl acetate/hexanes) to afford (S)—N-[5-((S)-2,2-dimethyl-[1,3]dioxolan-4-yl)-pyrazin-2-yl]-4-methylsulfanyl-2-(1-oxo-4-trifluoromethyl-1,3-dihydro-isoindol-2-yl)-butyramide (28 mg, 32%) as a colorless sticky solid.

A solution of (S)—N-[5-((S)-2,2-dimethyl-[1,3]dioxolan-4-yl)-pyrazin-2-yl]-4-methylsulfanyl-2-(1-oxo-4-trifluoromethyl-1,3-dihydro-isoindol-2-yl)-butyramide (26 mg, 0.05 mmol) in tetrahydrofuran (1 mL) was treated with a 1N aqueous hydrochloric acid solution (1 mL) and stirred at room temperature overnight. The reaction mixture was then concentrated in vacuo to remove the tetrahydrofuran and the remaining material was partitioned between ethyl acetate and a saturated aqueous sodium bicarbonate solution. The organic layer was separated and dried over magnesium sulfate, filtered to remove the drying agent and the filtrate concentrated in vacuo to afford (S)—N-[5-((S)-1,2-dihydroxy-ethyl)-pyrazin-2-yl]-4-methylsulfanyl-2-(1-oxo-4-trifluoromethyl-1,3-dihydro-isoindol-2-yl)-butyramide (20 mg, 85%) as a pale yellow gum: HR-ES(+) m/e calcd for $C_{20}H_{21}N_4O_4SF_3$ [M+H]$^+$ 471.1309, observed 471.1306; $^1$H NMR (400 MHz, DMSO-$d_6$) δ 11.15 (s, 1H), 9.16 (s, 1H), 8.44 (d, J=1.28 Hz, 1H), 8.02 (t, J=7.46 Hz, 2H), 7.71-7.81 (m, 1H), 5.55 (d, J=4.90 Hz, 1H), 5.18 (dd, J=5.01, 9.48 Hz, 1H), 4.93-5.02 (m, 1H), 4.77-4.87 (m, 1H), 4.72 (t, J=5.86 Hz, 1H), 4.58-4.66 (m, 1H), 3.61-3.71 (m, 1H), 3.55 (td, J=5.86, 11.29 Hz, 1H), 2.48-2.65 (m, 3H), 2.22-2.38 (m, 1H), 2.09 (s, 3H).

Example 23

(S)-4-Methyl-2-(1-oxo-4-trifluoromethyl-1,3-dihydro-isoindol-2-yl)-pentanoic acid pyrazin-2-ylamide

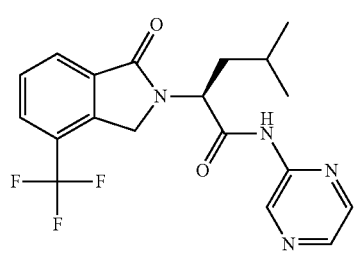 [SMILES: CC(C)C[C@@H](C(=O)Nc1cnccn1)N1Cc2c(cccc2C(F)(F)F)C1=O]

A mixture of (S)-2-amino-4-methyl-pentanoic acid methyl ester hydrochloride (Aldrich, 273 mg, 1.5 mmol) and 2-bromomethyl-3-trifluoromethyl-benzoic acid methyl ester (prepared as in Example 1, 445 mg, 1.5 mmol) in acetonitrile (5 mL) and triethylamine (420 μL, 3.0 mmol) was placed in a microwave reaction vessel and sealed. The reaction mixture was then placed in a microwave reactor and heated at 115° C. for 15 min. After this time, the reaction mixture was cooled and concentrated with silica gel (2 g) in vacuo. The silica gel with absorbed material was placed in a SIM and purified via Biotage flash column chromatography (40 S silica gel column, 20% ethyl acetate/hexanes) to afford (S)-4-methyl-2-(1-oxo-4-trifluoromethyl-1,3-dihydro-isoindol-2-yl)-pentanoic acid methyl ester (275 mg, 56%) as a colorless viscous oil.

A solution of (S)-4-methyl-2-(1-oxo-4-trifluoromethyl-1,3-dihydro-isoindol-2-yl)-pentanoic acid methyl ester (274 mg, 0.83 mmol) in tetrahydrofuran/water (12 mL, 1:1) was treated with lithium hydroxide monohydrate (70 mg, 1.66 mmol) at room temperature. The reaction mixture was then stirred at room temperature for 2 h. After this time, the reaction mixture was concentrated in vacuo to remove the tetrahydrofuran. The resulting material was then diluted with a 1N aqueous hydrochloric acid solution (10 mL) and then extracted with ethyl acetate. The organic layers were combined and then dried over magnesium sulfate, filtered to remove the drying agent, and the filtrate was concentrated in vacuo to afford (S)-4-methyl-2-(1-oxo-4-trifluoromethyl-1,3-dihydro-isoindol-2-yl)-pentanoic acid (254 mg, 97%) as a white solid.

A solution of (S)-4-methyl-2-(1-oxo-4-trifluoromethyl-1,3-dihydro-isoindol-2-yl)-pentanoic acid (95 mg, 0.30 mmol) in methylene chloride (5 mL) and N,N-dimethylformamide (5 drops) at room temperature was treated with a solution of oxalyl chloride (2.0M in methylene chloride, 200 μL, 0.36 mmol) and stirred for 15 min. After this time, the reaction mixture was concentrated in vacuo and then diluted with methylene chloride (5 mL) and added to a flask containing a solution of 2-aminopyrazine (Aldrich, 57 mg, 0.60 mmol), 2,6-lutidine (250 μL) in methylene chloride (2.5 mL) at 0° C. The reaction mixture was then stirred at room temperature for a period of 30 min After this time, the reaction mixture was treated with methanol and then diluted with methylene chloride. The reaction mixture was then transferred to a separatory funnel and washed with a 1N aqueous hydrochloric acid solution. The organic layer was then dried over magnesium sulfate, filtered to remove the drying agent and the filtrate was concentrated with silica gel (2 g). The silica gel with absorbed material was placed in a SIM and purified via Biotage flash column chromatography (40 S silica gel column, 25%-40% ethyl acetate/hexanes) to afford (S)-4-methyl-2-(1-oxo-4-trifluoromethyl-1,3-dihydro-isoindol-2-yl)-pentanoic acid pyrazin-2-ylamide (14 mg, 12%): HR-ES(+) m/e calcd for $C_{19}H_{19}N_4O_2F_3$ [M+H]$^+$ 393.1533, observed 393.1532; $^1$H NMR (400 MHz, CHLOROFORM-d) δ 9.49 (s, 1H), 9.03 (br. s., 1H), 8.29-8.38 (m, 2H), 8.10 (d, J=7.67 Hz, 1H), 7.84 (d, J=7.88 Hz, 1H), 7.65 (t, J=7.67 Hz, 1H), 5.14 (dd, J=6.93, 8.84 Hz, 1H), 4.69-4.82 (m, 1H), 4.58-4.67 (m, 1H), 1.88-2.15 (m, 2H), 1.62 (td, J=6.87, 13.96 Hz, 1H), 1.01-1.10 (m, 6H).

Example 24

(S)-4-Methyl-2-(1-oxo-4-trifluoromethyl-1,3-dihydro-isoindol-2-yl)-pentanoic acid [5-((S)-1,2-dihydroxy-ethyl)-pyrazin-2-yl]-amide

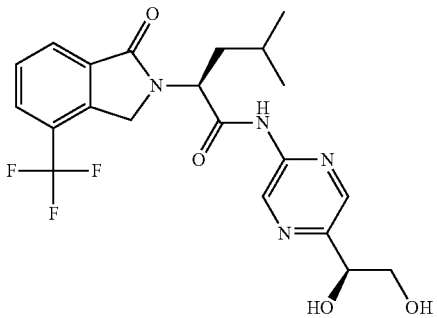 [SMILES: CC(C)C[C@@H](C(=O)Nc1cnc([C@H](O)CO)cn1)N1Cc2c(cccc2C(F)(F)F)C1=O]

A solution of (S)-4-methyl-2-(1-oxo-4-trifluoromethyl-1,3-dihydro-isoindol-2-yl)-pentanoic acid (prepared as in Example 23, 79 mg, 0.25 mmol) in methylene chloride (5 mL) and N,N-dimethylformamide (5 drops) at room temperature was treated with a solution of oxalyl chloride (2.0M in methylene chloride, 150 µL, 0.30 mmol) and stirred for 15 min. After this time, the reaction mixture was concentrated in vacuo and then diluted with methylene chloride (5 mL) and added to a flask containing a solution of 5-((S)-2,2-dimethyl-[1,3]dioxolan-4-yl)-pyrazin-2-ylamine (prepared as in WO2004052869, Example 54, 98 mg, 0.50 mmol), 2,6-lutidine (100 µL, 0.50 mmol) in methylene chloride (2.5 mL) at room temperature. The reaction mixture was then stirred at room temperature for a period of 2 h. After this time, the reaction mixture was treated with methanol and then diluted with methylene chloride. The reaction mixture was then transferred to a separatory funnel and washed with a 1N aqueous hydrochloric acid solution. The organic layer was then dried over magnesium sulfate, filtered to remove the drying agent and the filtrate was concentrated with silica gel (2 g). The silica gel with absorbed material was placed in a SIM and purified via Biotage flash column chromatography (40 S silica gel column, 40% ethyl acetate/hexanes) to afford (S)-4-methyl-2-(1-oxo-4-trifluoromethyl-1,3-dihydro-isoindol-2-yl)-pentanoic acid [5-((S)-2,2-dimethyl-[1,3]dioxolan-4-yl)-pyrazin-2-yl]-amide (54 mg, 44%) as a colorless sticky solid: HR-ES(+) m/e calcd for $C_{24}H_{27}N_4O_4F_3$ $[M+H]^+$ 493.2057, observed 493.2059; $^1$H NMR (400 MHz, CHLOROFORM-d) δ 9.37 (d, J=1.28 Hz, 1H), 8.83 (s, 1H), 8.44 (s, 1H), 8.08 (d, J=7.46 Hz, 1H), 7.82 (d, J=7.67 Hz, 1H), 7.64 (t, J=7.78 Hz, 1H), 5.20 (t, J=6.50 Hz, 1H), 5.13 (dd, J=6.93, 8.84 Hz, 1H), 4.68-4.78 (m, 1H), 4.55-4.65 (m, 1H), 4.42 (dd, J=6.82, 8.52 Hz, 1H), 3.95 (dd, J=6.29, 8.42 Hz, 1H), 2.00-2.13 (m, 1H), 1.88-2.00 (m, 1H), 1.53-1.69 (m, 1H), 1.44-1.52 (m, 6H), 0.97-1.07 (m, 6H).

A solution of afford (S)-4-methyl-2-(1-oxo-4-trifluoromethyl-1,3-dihydro-isoindol-2-yl)-pentanoic acid [5-((S)-2,2-dimethyl-[1,3]dioxolan-4-yl)-pyrazin-2-yl]-amide (53 mg, 0.11 mmol) in tetrahydrofuran (1 mL) was treated with a 1N aqueous hydrochloric acid solution (1 mL) and stirred at room temperature overnight. The reaction mixture was then concentrated in vacuo to remove the tetrahydrofuran and the remaining material was partitioned between ethyl acetate and a saturated aqueous sodium bicarbonate solution. The organic layer was separated and dried over magnesium sulfate, filtered to remove the drying agent and the filtrate concentrated in vacuo to afford (S)-4-methyl-2-(1-oxo-4-trifluoromethyl-1,3-dihydro-isoindol-2-yl)-pentanoic acid [5-((S)-1,2-dihydroxy-ethyl)-pyrazin-2-yl]-amide (43 mg, 88%) as a cream colored foam: $[α]^{29}_D$=+22.9° (c=0.14, methanol); HR-ES(+) m/e calcd for $C_{21}H_{23}N_4O_4F_3$ $[M+H]^+$ 453.1744, observed 453.1744; $^1$H NMR (400 MHz, DMSO-$d_6$) δ 11.26 (s, 1H), 9.16 (s, 1H), 8.45 (d, J=1.07 Hz, 1H), 8.02 (dd, J=7.67, 11.29 Hz, 2H), 7.67-7.85 (m, 1H), 5.55 (d, J=4.90 Hz, 1H), 5.28 (dd, J=5.11, 10.65 Hz, 1H), 5.05 (d, J=18.33 Hz, 1H), 4.66-4.78 (m, 2H), 4.62 (q, J=4.90 Hz, 1H), 3.67 (td, J=5.30, 10.92 Hz, 1H), 3.55 (td, J=5.78, 11.24 Hz, 1H), 1.95-2.09 (m, 1H), 1.71-1.88 (m, 1H), 1.49 (br. s., 1H), 0.90-1.00 (m, 6H).

Example 25

In Vitro Glucokinase Activity

The compounds of formula I, which include the compounds set forth in the Examples, were found to activate glucokinase in vitro by the procedure of this Example. In this manner, they increase the flux of glucose metabolism which causes increased insulin secretion. Therefore, the compounds of formula I are glucokinase activators useful for increasing insulin secretion.

Glucokinase In Vitro Assay Protocol:

Glucokinase (GK) was assayed by coupling the production of glucose-6-phosphate to the generation of NADH with glucose-6-phosphate dehydrogenase (G6PDH, 0.75-1 kunits/mg; Boehringer Mannheim, Indianapolis, *Leuconostoc mesenteroides* as the coupling enzyme (Scheme 2).

Scheme 2

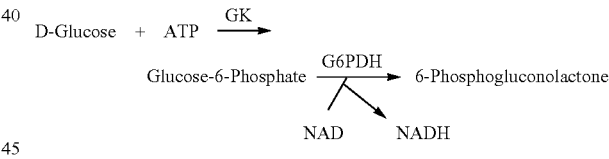

Recombinant human liver GK1 was expressed in *E. coli* as a glutathione S-transferase fusion protein (GST-GK) and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical.

The assay was conducted at 30° C. in a flat bottom 96-well tissue culture plate from Costar (Cambridge, Mass.) with a final incubation volume of 120 µL. The incubation reaction contained the following: 25 mM Hepes buffer (pH 7.1), 25 mM KCl, 5 mM D-glucose, 1 mM ATP, 1.8 mM NAD, 2 mM $MgCl_2$, 1 µM sorbitol-6-phosphate, 1 mM dithiothreitol, test drug or 10% dimethylsulfoxide, ~7 units/ml G6PDH, and GK (see below). All organic reagents were >98% pure and were from Boehringer Mannheim with the exceptions of D-glucose and Hepes which were from Sigma Chemical Co, St Louis, Mo. Test compounds were dissolved in dimethylsulfoxide and were added to the incubation reaction minus GST-GK in a volume of 12 µL to yield a final dimethylsulfoxide concentration of 10%. This mix was pre-incubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 μL GST-GK.

After addition of enzyme, the increase in optical density (OD) at 340 nm was monitored spectrophotometrically to determine the rate of change ($OD_{340}$ per min). The GK activity ($OD_{340}$/min) in control wells (10% dimethylsulfoxide minus GK activators) was compared with the activity in wells containing test GK activators, and the concentration of activator that produced a 50% increase in the activity of GK, i.e., the $SC_{1.5}$, was calculated.

Table 1 below provides the in vitro glucokinase activity for the compounds in the Examples:

TABLE 1

| Example | SC1.5 (μM) |
|---|---|
| 1 | 0.187 |
| 2 | 0.186 |
| 3 | 0.244 |
| 4 | 0.439 |
| 5 | 0.074 |
| 6 | 0.119 |
| 7 | 0.032 |
| 8 | 3.526 |
| 9 | 1.6 |
| 10 | 20.625 |
| 11 | 2.091 |
| 12 | 1.857 |
| 13 | 0.328 |
| 14 | 1.242 |
| 15 | 0.176 |
| 16 | 0.062 |
| 17 | 0.179 |
| 18 | 0.962 |
| 19 | 0.334 |
| 20 | 0.457 |
| 21 | 0.255 |
| 22 | 14.914 |
| 23 | 1.422 |
| 24 | 2.966 |

Example 26

In Vivo Glucokinase Activity

Glucokinase Activator In Vivo Screen Protocol in Lean Mice:

Lean C57BL/6J mice were orally dosed via gavage with Glucokinase (GK) activator following a two hour fasting period. Blood glucose determinations were made at various (e.g. 0, 1, 2, 4 and 8 hours post-oral gavage) times during the study.

C57B1/6J mice were obtained from Jackson Laboratory (Bar Harbor, Me.) and were maintained in a light-dark cycle with lights on from 0600-1800 hr. For studies in lean mice, the mice were received at age ten weeks and given ad libitum access to control diet (LabDiet 5001 chow, PMI Nutrition, Brentwood, Mo.), and were at least age 11 weeks at the time of study. For studies in the DIO model, the mice were received at age five weeks and given ad libitum access to Bio-Sery F3282 High Fat Diet (Frenchtown, N.J.), and were at least age 16 weeks at the time of study. The experiments were conducted during the light phase of the light-dark cycle. Mice (n=6) are weighed and fasted for a two hour period prior to oral treatment. GK activators are formulated in Gelucire vehicle (Ethanol:Gelucire44/14:PEG400q.s. 4:66:30 v/w/v). For studies in lean mice, the mice were dosed orally with 5.0 μL per gram of body weight (i.e. 5 ml/kg×10.0 mg/ml formulation to equal a 50 mg/kg dose). For studies in DIO mice, the mice were dosed orally with 5.0 μL per gram of body weight (i.e. 5.0 ml/kg×5 mg/ml formulation to equal a 25 mg/kg dose). Immediately prior to dosing, a pre-dose (time zero) blood glucose reading was acquired by snipping off a small portion of the animal's tail and collecting 15 μL blood into a heparinized capillary tube for analysis. Following GK activator administration, additional blood glucose readings were taken at various time points post dose from the same tail wound. Results were interpreted by comparing the mean blood glucose values of vehicle treated mice with GK activator treated mice over the study period. Preferred compounds were considered to be those that exhibited a statistically significant (p≦0.05) decrease in blood glucose compared to vehicle for two consecutive assay time points.

Table 2 below provides data for % glucose lowering of a representative number of compounds of the present invention vs. control at 2 hours post 25 or 50 mg/kg dose in C57B6 mice:

TABLE 2

| Exampl | % gluc lowering @ 2 H | Dose (mg/K) |
|---|---|---|
| 1 | −39.8 | 25 |
| 2 | −38.8 | 25 |
| 5 | −50.1 | 25 |
| 6 | −48.3 | 25 |
| 7 | −48.2 | 25 |
| 13 | −45.2 | 50 |
| 15 | −22.5 | 25 |
| 17 | −40.2 | 25 |
| 18 | −25.4 | 25 |
| 21 | −36.6 | 25 |

It is to be understood that the invention is not limited to the particular embodiments of the invention described above, as variations of the particular embodiments may be made and still fall within the scope of the appended claims.

The invention claimed is:

1. A compound according to formula (I),

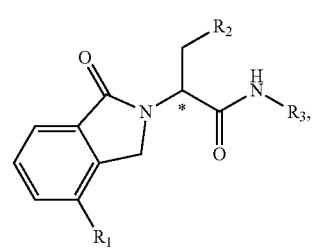

(I)

wherein:
$R_1$ is selected from the group consisting of: H, F, and $CF_3$;
$R_2$ is selected from the group consisting of: cyclopropyl, cyclopentyl and cyclohexyl;
$R_3$ is

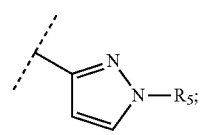

and

R₅ is selected from the group consisting of: —CH(OH)—CH₂OH, —CH₂—C(CH₃)₂—O—CH₃, —CH₂—CH₂OH, —CH₂—C(O)—O—C(CH₃)₃, —(CH₂)₂O—CH₃, —CH₂—COOH, —(CH₂)₂—COOH, —(CH₂)₂—C(O)—O—C(CH₃)₃, —(CH₂)₂—CH₂OH, —(CH₂)₂—O—CH(CH₃)₂, and —CH₃;

or a pharmaceutically-active salt of said compound.

2. A compound according to claim 1, selected from the group consisting of:
- (S)-3-cyclopentyl-N-(1-methyl-1H-pyrazol-3-yl)-2-(1-oxo-4-trifluoromethyl-1,3-dihydro-isoindol-2-yl)-propionamide;
- (S)-3-cyclopentyl-N-[1-(2-hydroxy-ethyl)-1H-pyrazol-3-yl]-2-(1-oxo-4-trifluoromethyl-1,3-dihydro-isoindol-2-yl)-propionamide;
- {3-[(S)-3-cyclopentyl-2-(1-oxo-4-trifluoromethyl-1,3-dihydro-isoindol-2-yl)-propionylamino]-pyrazol-1-yl}-acetic acid tert-butyl ester;
- {3-[(S)-3-cyclopentyl-2-(1-oxo-4-trifluoromethyl-1,3-dihydro-isoindol-2-yl)-propionylamino]-pyrazol-1-yl}-acetic acid;
- (S)-3-cyclopentyl-N-[1-((R)-2,3-dihydroxy-propyl)-1H-pyrazol-3-yl]-2-(1-oxo-4-trifluoromethyl-1,3-dihydro-isoindol-2-yl)-propionamide;
- (S)-3-cyclopentyl-N-[1-((S)-2,3-dihydroxy-propyl)-1H-pyrazol-3-yl]-2-(1-oxo-4-trifluoromethyl-1,3-dihydro-isoindol-2-yl)-propionamide;
- (S)-3-cyclopentyl-N-[1-(2-methoxy-2-methyl-propyl)-1H-pyrazol-3-yl]-2-(1-oxo-4-trifluoromethyl-1,3-dihydro-isoindol-2-yl)-propionamide;
- (S)-3-cyclohexyl-N-[1-(2-methoxy-ethyl)-1H-pyrazol-3-yl]-2-(1-oxo-1,3-dihydro-isoindol-2-yl)-propionamide;
- (S)-3-cyclopentyl-N-[1-(2-methoxy-ethyl)-1H-pyrazol-3-yl]-2-(1-oxo-1,3-dihydro-isoindol-2-yl)-propionamide;
- (S)-3-cyclopropyl-N-[1-(2-methoxy-2-methyl-propyl)-1H-pyrazol-3-yl]-2-(1-oxo-1,3-dihydro-isoindol-2-yl)-propionamide;

and pharmaceutically-acceptable salts thereof.

3. A compound according to claim 1, selected from the group consisting of:
- (S)-3-cyclopentyl-N-[1-(2-isopropoxy-ethyl)-1H-pyrazol-3-yl]-2-(1-oxo-1,3-dihydro-isoindol-2-yl)-propionamide;
- (S)-3-cyclopentyl-N-[1-(3-hydroxy-propyl)-1H-pyrazol-3-yl]-2-(1-oxo-1,3-dihydro-isoindol-2-yl)-propionamide;
- (S)-3-cyclopentyl-N-[1-(2-methoxy-ethyl)-1H-pyrazol-3-yl]-2-(1-oxo-4-trifluoromethyl-1,3-dihydro-isoindol-2-yl)-propionamide;
- (S)-3-cyclopentyl-N-[1-(2-methoxy-2-methyl-propyl)-1H-pyrazol-3-yl]-2-(1-oxo-1,3-dihydro-isoindol-2-yl)-propionamide;
- (S)-3-cyclopentyl-N-[1-(2-isopropoy-ethyl)-1H-pyrazol-3-yl]-2-(1-oxo-4-trifluoromethyl-1,3-dihydro-isoindol-2-yl)-propionamide;
- (S)-3-cyclohexyl-2-(4-fluoro-1-oxo-1,3-dihydro-isoindol-2-yl)-N-[1-(2-methoxy-ethyl)-1H-pyrazol-3-yl]-propionamide;
- 3-{3-[(S)-3-cyclopentyl-2-(1-oxo-4-trifluoromethyl-1,3-dihydro-isoindol-2-yl)-propionylamino]-pyrazol-1-yl}-propionic acid tert-butyl ester;
- 3-{3-[(S)-3-cyclopentyl-2-(1-oxo-4-trifluoromethyl-1,3-dihydro-isoindol-2-yl)-propionylamino]-pyrazol-1-yl}-propionic acid;

and pharmaceutically-acceptable salts thereof.

4. A compound according to claim 1, wherein R₁ is CF₃.

5. A compound according to claim 4, selected from the group consisting of:
- (S)-3-cyclopentyl-N-(1-methyl-1H-pyrazol-3-yl)-2-(1-oxo-4-trifluoromethyl-1,3-dihydro-isoindol-2-yl)-propionamide;
- (S)-3-cyclopentyl-N-[1-(2-hydroxy-ethyl)-1H-pyrazol-3-yl]-2-(1-oxo-4-trifluoromethyl-1-1,3-dihydro-isoindol-2-yl)-propionamide;
- {3-[(S)-3-cyclopentyl-2-(1-oxo-4-trifluoromethyl-1,3-dihydro-isoindol-2-yl)-propionylamino]-pyrazol-1-yl}-acetic acid tert-butyl ester;
- {3-[(S)-3-cyclopentyl-2-(1-oxo-4-trifluoromethyl-1,3-dihydro-isoindol-2-yl)-propionylamino]-pyrazol-1-yl}-acetic acid;
- (S)-3-cyclopentyl-N-[1-((R)-2,3-dihydroxy-propyl)-1H-pyrazol-3-yl]-2-(1-oxo-4-trifluoromethyl-1,3-dihydro-isoindol-2-yl)-propionamide;
- (S)-3-cyclopentyl-N-[1-((S)-2,3-dihydroxy-propyl)-1H-pyrazol-3-yl]-2-(1-oxo-4-trifluoromethyl-1,3-dihydro-isoindol-2-yl)-propionamide;
- (S)-3-cyclopentyl-N-[1-(2-methoxy-2-methyl-propyl)-1H-pyrazol-3-yl]-2-(1-oxo-4-trifluoromethyl-1,3-dihydro-isoindol-2-yl)-propionamide;
- (S)-3-cyclopentyl-N-[1-(2-methoxy-ethyl)-1H-pyrazol-3-yl]-2-(1-oxo-4-trifluoromethyl-1,3-dihydro-isoindol-2-yl)-propionamide;

and pharmaceutically-acceptable salts thereof.

6. A compound according to claim 4, selected from the group consisting of:
- (S)-3-cyclopentyl-N-[1-(2-isopropoy-ethyl)-1H-pyrazol-3-yl]-2-(1-oxo-4-trifluoromethyl-1,3-dihydro-isoindol-2-yl)-propionamide;
- 3-{3-[(S)-3-cyclopentyl-2-(1-oxo-4-trifluoromethyl-1,3-dihydro-isoindol-2-yl)-propionylamino]-pyrazol-1-yl}-propionic acid tert-butyl ester;
- 3-{3-[(S)-3-cyclopentyl-2-(1-oxo-4-trifluoromethyl-1,3-dihydro-isoindol-2-yl)-propionylamino]-pyrazol-1-yl}-propionic acid;

and pharmaceutically-acceptable salts thereof.

7. A compound according to claim 1, wherein R₂ is cyclopentyl.

8. A compound according to claim 7, selected from the group consisting of:
- (S)-3-cyclopentyl-N-(1-methyl-1H-pyrazol-3-yl)-2-(1-oxo-4-trifluoromethyl-1,3-dihydro-isoindol-2-yl)-propionamide;
- (S)-3-cyclopentyl-N-[1-(2-hydroxy-ethyl)-1H-pyrazol-3-yl]-2-(1-oxo-4-trifluoromethyl-1,3-dihydro-isoindol-2-yl)-propionamide;
- {3-[(S)-3-cyclopentyl-2-(1-oxo-4-trifluoromethyl-1,3-dihydro-isoindol-2-yl)-propionylamino]-pyrazol-1-yl}-acetic acid tert-butyl ester;
- {3-[(S)-3-cyclopentyl-2-(1-oxo-4-trifluoromethyl-1,3-dihydro-isoindol-2-yl)-propionylamino]-pyrazol-1-yl}-acetic acid;
- (S)-3-cyclopentyl-N-[1-((R)-2,3-dihydroxy-propyl)-1H-pyrazol-3-yl]-2-(1-oxo-4-trifluoromethyl-1,3-dihydro-isoindol-2-yl)-propionamide;
- (S)-3-cyclopentyl-N-[1-((S)-2,3-dihydroxy-propyl)-1H-pyrazol-3-yl]-2-(1-oxo-4-trifluoromethyl-1,3-dihydro-isoindol-2-yl)-propionamide;
- (S)-3-cyclopentyl-N-[1-(2-methoxy-2-methyl-propyl)-1H-pyrazol-3-yl]-2-(1-oxo-4-trifluoromethyl-1,3-dihydro-isoindol-2-yl)-propionamide;
- (S)-3-cyclopentyl-N-[1-(2-methoxy-ethyl)-1H-pyrazol-3-yl]-2-(1-oxo-1,3-dihydro-isoindol-2-yl)-propionamide;

(S)-3-cyclopentyl-N-[1-(2-isopropoxy-ethyl)-1H-pyrazol-3-yl]-2-(1-oxo-1,3-dihydro-isoindol-2-yl)-propionamide;

(S)-3-cyclopentyl-N-[1-(3-hydroxy-propyl)-1H-pyrazol-3-yl]-2-(1-oxo-1,3-dihydro-isoindol-2-yl)-propionamide;

and pharmaceutically-acceptable salts thereof.

9. A compound according to claim j), selected from the group consisting of:

(S)-3-cyclopentyl-N-[1-(2-methoxy-ethyl)-1H-pyrazol-3-yl]-2-(1-oxo-4-trifluoromethyl-1,3-dihydro-isoindol-2-yl)-propionamide;

(S)-3-cyclopentyl-N-[1-(2-methoxy-2-methyl-propyl)-1H-pyrazol-3-yl]-2-(1-oxo-1,3-dihydro-isoindol-2-yl)-propionamide;

(S)-3-cyclopentyl-N-[1-(2-isopropoy-ethyl)-1H-pyrazol-3-yl]-2-(1-oxo-4-trifluoromethyl-1,3-dihydro-isoindol-2-yl)-propionamide;

3-{3-[(S)-3-cyclopentyl-2-(1-oxo-4-trifluoromethyl-1,3-dihydro-isoindol-2-yl)-propionylamino]-pyrazol-1-yl}-propionic acid tert-butyl ester;

3-{3-[(S)-3-cyclopentyl-2-(1-oxo-4-trifluoromethyl-1,3-dihydro-isoindol-2-yl)-propionylamino]-pyrazol-1-yl}-propionic acid;

and pharmaceutically-acceptable salts thereof.

10. A compound according to claim 1 wherein $R_1$ is H.

11. A compound according to claim 10, wherein said compound is selected from the group consisting of:

(S)-3-cyclohexyl-N-[1-(2-methoxy-ethyl)-1H-pyrazol-3-yl]-2-(1-oxo-1,3-dihydro-isoindol-2-yl)-propionamide;

(S)-3-cyclopentyl-N-[1-(2-methoxy-ethyl)-1H-pyrazol-3-yl]-2-(1-oxo-1,3-dihydro-isoindol-2-yl)-propionamide;

(S)-3-cyclopropyl-N-[1-(2-methoxy-2-methyl-propyl)-1H-pyrazol-3-yl]-2-(1-oxo-1,3-dihydro-isoindol-2-yl)-propionamide;

(S)-3-cyclopentyl-N-[1-(2-isopropoxy-ethyl)-1H-pyrazol-3-yl]-2-(1-oxo-1,3-dihydro-isoindol-2-yl)-propionamide;

(S)-3-cyclopentyl-N-[1-(3-hydroxy-propyl)-1H-pyrazol-3-yl]-2-(1-oxo-1,3-dihydro-isoindol-2-yl)-propionamide;

(S)-3-cyclopentyl-N-[1-(2-methoxy-2-methyl-propyl)-1H-pyrazol-3-yl]-2-(1-oxo-1,3-dihydro-isoindol-2-yl)-propionamide;

and pharmaceutically-acceptable salts thereof.

12. A compound according to claim 7, wherein said compound is selected from the group consisting of:

(S)-3-cyclopentyl-N-(1-methyl-1H-pyrazol-3-yl)-2-(1-oxo-4-trifluoromethyl-1,3-dihydro-isoindol-2-yl)-propionamide;

(S)-3-cyclopentyl-N-[1-(2-hydroxy-ethyl)-1H-pyrazol-3-yl]-2-(1-oxo-4-trifluoromethyl-1,3-dihydro-isoindol-2-yl)-propionamide;

{3-[(S)-3-cyclopentyl-2-(1-oxo-4-trifluoromethyl-1,3-dihydro-isoindol-2-yl)-propionylamino]-pyrazol-1-yl}-acetic acid tert-butyl ester;

{3-[(S)-3-cyclopentyl-2-(1-oxo-4-trifluoromethyl-1,3-dihydro-isoindol-2-yl)-propionylamino]-pyrazol-1-yl}-acetic acid;

(S)-3-cyclopentyl-N-[1-((R)-2,3-dihydroxy-propyl)-1H-pyrazol-3-yl]-2-(1-oxo-4-trifluoromethyl-1,3-dihydro-isoindol-2-yl)-propionamide;

(S)-3-cyclopentyl-N-[1-((S)-2,3-dihydroxy-propyl)-1H-pyrazol-3-yl]-2-(1-oxo-4-trifluoromethyl-1,3-dihydro-isoindol-2-yl)-propionamide;

(S)-3-cyclopentyl-N-[1-(2-methoxy-2-methyl-propyl)-1H-pyrazol-3-yl]-2-(1-oxo-4-trifluoromethyl-1,3-dihydro-isoindol-2-yl)-propionamide;

(S)-3-cyclopentyl-N-[1-(2-methoxy-ethyl)-1H-pyrazol-3-yl]-2-(1-oxo-4-trifluoromethyl-1-1,3-dihydro-isoindol-2-yl)-propionamide;

(S)-3-cyclopentyl-N-[1-(2-isopropoy-ethyl)-1H-pyrazol-3-yl]-2-(1-oxo-4-trifluoromethyl-1,3-dihydro-isoindol-2-yl)-propionamide;

3-{3-[(S)-3-cyclopentyl-2-(1-oxo-4-trifluoromethyl-1,3-dihydro-isoindol-2-yl)-propionylamino]-pyrazol-1-yl}-propionic acid tert-butyl ester;

3-{3-[(S)-3-cyclopentyl-2-(1-oxo-4-trifluoromethyl-1,3-dihydro-isoindol-2-yl)-propionylamino]-pyrazol-1-yl}-propionic acid;

and pharmaceutically-acceptable salts thereof.

13. A pharmaceutical composition, comprising a compound according claim 1 and a pharmaceutically-acceptable carrier.

* * * * *